[19] United States Patent
Imaizumi et al.

[11] Patent Number: 5,366,989
[45] Date of Patent: Nov. 22, 1994

[54] TRIAZOLE DERIVATIVES AND SALTS THEREOF AND ANTIFUNGAL AGENT CONTAINING THE SAME

[75] Inventors: Hiroyuki Imaizumi, Toyama; Tetsuya Kajita, Takaoka; Kenichi Takashima, Oyabe; Minako Yotsuji, Toyama; Keiko Takakura, Toyama; Akira Yotsuji, Toyama; Junichi Mitsuyama, Toyama; Katsumi Shimizu, Toyama; Hiroshi Sakai, Takaoka; Hirokazu Narita, Toyama, all of Japan

[73] Assignee: Toyama Chemical Co., Ltd., Tokyo, Japan

[21] Appl. No.: 986,800

[22] Filed: Dec. 8, 1992

[30] Foreign Application Priority Data

Dec. 9, 1991 [JP] Japan .................................. 3-350318
Oct. 8, 1992 [JP] Japan .................................. 4-293961

[51] Int. Cl.$^5$ .................. A01N 43/653; C07D 249/08
[52] U.S. Cl. ............................ 514/383; 548/267.4; 548/267.6; 548/268.6
[58] Field of Search ............... 548/267.4, 267.6, 268.6; 514/383

[56] References Cited

U.S. PATENT DOCUMENTS

| | | | |
|---|---|---|---|
| 4,503,063 | 3/1985 | Richardson et al. | 514/383 |
| 4,518,604 | 5/1985 | Richardson et al. | 514/340 |
| 4,616,026 | 10/1986 | Richardson et al. | 514/381 |
| 4,616,027 | 10/1986 | Richardson et al. | 514/383 |
| 4,960,782 | 10/1990 | Gymer et al. | 514/383 |
| 5,047,548 | 9/1991 | Richardson et al. | 548/267.6 |

FOREIGN PATENT DOCUMENTS

| | | |
|---|---|---|
| 0106515 | 4/1984 | European Pat. Off. |
| 0117100 | 8/1984 | European Pat. Off. |
| 0136063 | 4/1985 | European Pat. Off. |
| 0235877 | 9/1987 | European Pat. Off. |
| 0313981 | 5/1989 | European Pat. Off. |
| 2132195 | 7/1984 | United Kingdom . |

OTHER PUBLICATIONS

Burger, "Medicinal Chemistry", 2nd Ed. NY 1960, p. 1055.

*Primary Examiner*—Patricia L. Morris
*Attorney, Agent, or Firm*—Oblon, Spivak, McClelland, Maier & Neustadt

[57] ABSTRACT

The present invention relates to a compound represented by the general formula (1) or its salt, a process for producing the same, and an antifungal agent comprising the same as an effective component:

$$\underset{N}{\overset{N=}{\underset{\Vert}{\bigsqcup}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!} \text{N—CH}_2\text{—}\overset{\overset{OH}{|}}{\underset{\underset{R^1}{|}}{C}}\text{—}\overset{\overset{F}{|}}{\underset{\underset{R^2}{|}}{C}}\text{—R}^3 \quad (1)$$

wherein $R^1$ represents a substituted or unsubstituted aryl group or a substituted or unsubstituted heterocyclic group bonded through a carbon atom in the ring to the main chain; $R^2$ presents a hydrogen atom, a fluorine atom or a substituted or unsubstituted alkyl group; and $R^3$ represents a cyano group, a thioamido group or a group represented by the formula $$-\overset{\overset{O}{\Vert}}{C}-R^4, \quad -\overset{\overset{NH}{\Vert}}{C}-R^5 \quad \text{or} \quad -\overset{\overset{NOR^6}{\Vert}}{C}-NH_2$$

in which $R^4$ is a hydroxyl group or a group of the formula $$-N\!\!\begin{array}{c}\diagup R^7 \\ \diagdown R^8\end{array}$$

($R^7$ and $R^8$, which may be the same or different, are hydrogen atoms or substituted or unsubstituted alkyl, alkenyl, alkynyl, cycloalkyl, aryl, amino, alkoxy, hydroxyl or heterocyclic groups, and may form a substi- (Abstract continued on next page.)

tuted or unsubstituted heterocyclic group together with the nitrogen atom to which $R^7$ and $R^8$ attach), $R^5$ is a substituted or unsubstituted alkoxy group or a group of the formula
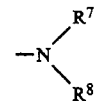
($R^7$ and $R^8$ are as defined above), and $R^6$ is a hydrogen atom or a substituted or unsubstituted alkyl group.
21 Claims, No Drawings

TRIAZOLE DERIVATIVES AND SALTS THEREOF AND ANTIFUNGAL AGENT CONTAINING THE SAME

The present invention relates to a novel triazole derivative or a salt thereof, a process for producing the same, and an antifungal agent containing the same.

Currently, Amphotericin B (disclosed in U.S. Pat. No. 2,908,611) and Flucytosine (disclosed in U.S. Pat. No. 2,802,005) are mainly used as remedies for deep mycosis. Further, Ketoconazole (disclosed in Japanese Patent Application Kokai (Laid-Open) No. 53-95973), Fluconazole (disclosed in Japanese Patent Application Kokai (Laid-Open) No. 58-32868), etc. are on the market as azole type antifungal agents. They are useful remedies for mycosis.

The above remedies, however, are not satisfactory in view of pharmacokinetics, toxicity, broad antifungal spectrum, etc. Hence, it has been desired to develop a more effective compound.

Under such circumstances, the present inventors have made extensive research and, as a result, found that the compound of the present invention has an excellent antifungal activity and exhibits an excellent therapeutic effect.

An object of the present invention is to provide a novel triazole derivative or a salt thereof.

Another object of the present invention is to provide a novel triazole derivative or a salt thereof, each having an excellent antifungal activity, being excellent in absorbability and exhibiting excellent pharmacokinetics.

Still another object of the present invention is to provide a process for producing a novel triazole derivative or a salt thereof.

A further object of the present invention is to provide an antifungal agent containing a novel triazole derivative or a salt thereof, each useful for the treatment of mycosis.

Other objects and advantages of the present invention will become apparent from the following description.

According to the present invention, there is provided a triazole derivative represented by the general formula (1) or a salt thereof:

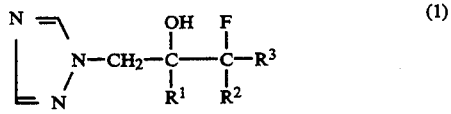

wherein $R^1$ represents a substituted or unsubstituted aryl group or a substituted or unsubstituted heterocyclic group bonded through a carbon atom in the ring to the main chain; $R^2$ represents a hydrogen atom, a fluorine atom or a substituted or unsubstituted alkyl group; and $R^3$ represents a cyano group, a thioamido group or a group represented by the formula

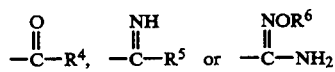

in which $R^4$ is a hydroxyl group or a group of the formula

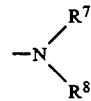

($R^7$ and $R^8$, which may be the same or different, are hydrogen atoms or substituted or unsubstituted alkyl, alkenyl, alkynyl, cycloalkyl, aryl, amino, alkoxy, hydroxyl or heterocyclic groups, and may form a substituted or unsubstituted heterocyclic group together with the nitrogen atom to which $R^7$ and $R^8$ attach), $R^5$ is a substituted or unsubstituted alkoxy group or a group of the formula

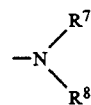

($R^7$ and $R^8$ are as defined above), and $R^6$ is a hydrogen atom or a substituted or unsubstituted alkyl group.

The compound of the present invention is hereinafter described in detail.

In the present specification, unless otherwise specified, the halogen atom means a fluorine atom, a chlorine atom, a bromine atom and an iodine atom: the alkyl group means a straight chain or branched chain $C_{1-10}$alkyl group such as methyl, ethyl, n-propyl, isopropyl, n-butyl, isobutyl, sec-butyl, tert-butyl, pentyl, hexyl, heptyl, octyl or the like; the alkenyl group means a straight chain or branched chain $C_{2-10}$alkenyl group such as vinyl, allyl, propenyl, isopropenyl, butenyl, isobutenyl, pentenyl, hexenyl or the like; the alkynyl group means a straight chain or branched chain $C_{2-10}$alkynyl group such as ethynyl, propynyl, butynyl, pentynyl, hexynyl or the like; the alkoxy group means a $C_{1-10}$alkoxy group such as methoxy, ethoxy, n-propoxy, isopropoxy, n-butoxy, isobutoxy, sec-butoxy, tert-butoxy, pentyloxy, hexyloxy, heptyloxy, octyloxy or the like; the lower alkoxycarbonyl group means a $C_{1-4}$alkoxycarbonyl group such as methoxycarbonyl, ethoxycarbonyl, n-propoxycarbonyl, isopropoxycarbonyl, n-butoxycarbonyl, isobutoxycarbonyl, secbutoxycarbonyl, tert-butoxycarbonyl or the like; the alkylthio group means a $C_{1-10}$alkylthio group such as methylthio, ethylthio, n-propylthio, isopropylthio, n-butylthio, isobutylthio, sec-butylthio, tert-butylthio, pentylthio, hexylthio, heptylthio, octylthio or the like; the aryl group means a phenyl or naphthyl group; the cycloalkyl group means a $C_{3-8}$cycloalkyl group such as cyclopropyl, cyclobutyl, cyclopentyl, cycloheptyl or the like; the halo-lower alkyl group means a halogen atom-substituted $C_{1-4}$alkyl group such as fluoromethyl, chloromethyl, trifluoromethyl, trichloromethyl, 2,2,2-trifluoroethyl, 1,1,2,2,2-pentafluoroethyl, 1,1,2,2,3,3,3-heptafluoropropyl or the like; the halo-lower alkoxy group means a halogen-substituted $C_{1-4}$alkoxy group such as fluoromethoxy, chloromethoxy, trifluoromethoxy, trichloromethoxy, 2,2,2-trifluoroethoxy, 1,1,2,2,2-pentafluoroethoxy, 1,1,2,2,3,3,3-heptafluoropropoxy or the like; the N-lower alkylamino group means an $N-C_{1-4}$alkylamino group such as methylamino, ethylamino, n-propylamino, isopropylamino, n-butylamino, isobutylamino, sec-butylamino, tert-butylamino or the like; the N,N-di-lower alkylamino group means an N,N-di-$C_{1-4}$alkylamino group such as dimethylamino, diethylamino, dipropylamino, methylethylamino or the like; the acyl group means a formyl group, a $C_{2-10}$alkanoyl group such as acetyl, ethylcarbonyl or the like, or an aroyl group such as benzoyl, naphthylcarbonyl or the like; and "lower" means a group having 1-4 carbon atoms.

In the definition of $R^1$, the heterocyclic group bonded through a carbon atom in the ring to the main chain of the triazole derivative includes five- and six-membered heterocyclic groups each containing at least one oxygen, sulfur or nitrogen atom, such as 2-furyl, 3-furyl, 2-thienyl, 3-thienyl, 2H-pyran-3-yl, pyrrol-3-yl, imidazol-2-yl, thiazol-2-yl, thiazol-4-yl, isothiazol-3-yl, isoxazol-3-yl, pyridin-2-yl, pyridin-3-yl, 1-oxidopyridin-3-yl, pyrazin-2-yl, pyrimidin-2-yl, pyrrolidin-2-yl, 2-pyrrolin-3-yl, imidazolidin-2-yl, 2-imidazolin-4-yl, piperidin-2-yl, morpholin-3-yl and the like.

In the definitions of $R^7$ and $R^8$, the heterocyclic group includes five- and six-membered heterocyclic groups each containing at least one oxygen, sulfur or nitrogen atom, such as thienyl, furyl, imidazolyl, triazolyl, pyrazolyl, thiazolyl, iso-thiazolyl, oxazolyl, isoxazolyl, thiadiazolyl, pyridyl, pyridazinyl, pyrimidinyl, pyrazinyl, triazinyl and the like. The substituted or unsubstituted heterocyclic group which $R^7$ and $R^8$ form together with the nitrogen atom to which $R^7$ and $R^8$ attach, includes three- to six-membered nitrogen-containing heterocyclic groups such as aziridinyl, azetidinyl, pyrrolidinyl, piperidinyl, morpholinyl, piperazinyl and the like.

Each of the substituted aryl group and the substituted heterocyclic group bonded through a carbon atom in the ring to the main chain in the definition of $R^1$; the substituted alkyl group in the definitions of $R^2$ and $R^6$; the substituted alkyl, alkenyl, alkynyl, cycloalkyl, aryl, amino, alkoxy, hydroxyl and heterocyclic groups in the definitions of $R^7$ and $R^8$; the substituted heterocyclic group which $R^7$ and $R^8$ form together with the nitrogen atom to which $R^7$ and $R^8$ attach in the definitions of $R^7$ and $R^8$; and the substituted alkoxy group in the definition of $R^5$ has at least one substituent selected from the group consisting of halogen atoms, unsubstituted or cyano-substituted lower alkyl groups, lower alkoxy groups, halo-lower alkoxy groups, lower alkylthio groups, lower alkoxycarbonyl groups, hydroxyl group, mercapto group, carboxyl group, amino group, N-lower alkylamino groups, N,N-di-lower alkylamino groups, cyano group, nitro group, halo-lower alkyl groups, unsubstituted or halogen-substituted aryl groups, unsubstituted or halogen-substituted acyl groups and unsubstituted or alkyl-, cycloalkyl- or aryl-substituted carbamoyl groups.

Of the compounds of the general formula (1), preferable are those compounds wherein $R^1$ is a halogen-substituted phenyl group, $R^2$ is a fluorine atom, and $R^3$ is a group of the formula

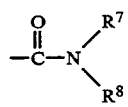

(one of $R^7$ and $R^8$ is a hydrogen atom and the other is a hydrogen atom, a lower alkyl group or a cyclopropyl group); more preferable are those compounds wherein $R^1$ is a 2,4-difluorophenyl group or a 2-chloro-4-fluorophenyl group, $R^2$ is a fluorine atom, and $R^3$ is a group of the formula

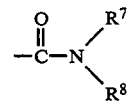

(one of $R^7$ and $R^8$ is a hydrogen atom and the other is a hydrogen atom, a methyl group or a cyclopropyl group), or optically active compounds corresponding thereto.

The salt of the compound of the general formula (1) includes pharmaceutically acceptable salts, for example, salts with mineral acids such as hydrochloric acid, sulfuric acid, nitric acid, phosphoric acid and the like; salts with carboxylic acids such as acetic acid, fumaric acid, maleic acid, malic acid, tartaric acid, citric acid, oxalic acid, aspartic acid and the like; and salts with sulfonic acids such as methanesulfonic acid, benzenesulfonic acid, toluenesulfonic acid and the like.

The compound of the present invention further includes all geometrical and optical isomers, hydrates and solvates, and also includes all crystal forms.

The novel triazole derivative of the general formula (1) and its salt can generally be produced by a process known per se or a combination thereof. They can be produced by, for example, one of following Processes 1 to 8:

Process 1

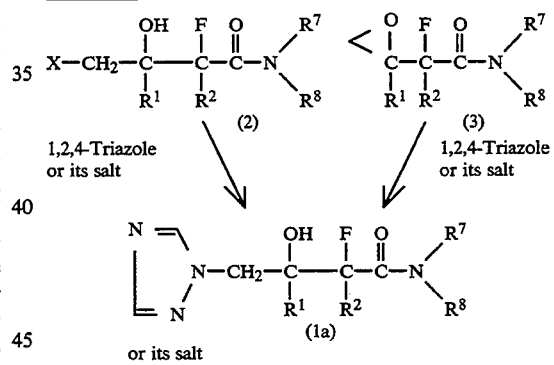

wherein X represents a removable group, for example, a halogen atom; a lower alkylsulfonyloxy group such as methanesulfonyloxy, ethanesulfonyloxy or the like; or an unsubstituted or halogen- or lower-alkyl-substituted arylsulfonyloxy group such as benzenesulfonyloxy, tosyloxy, p-chlorobenzenesulfonyloxy or the like, and $R^1$, $R^2$, $R^7$ and $R^8$ have the same meanings as defined above.

Process 2

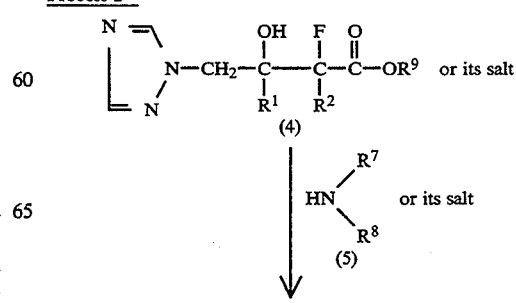

Process 2

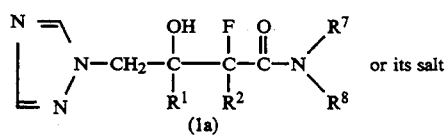

wherein $R^9$ represents a lower alkyl group; and $R^1$, $R^2$, $R^7$ and $R^8$ have the same meanings as defined above.

Process 3

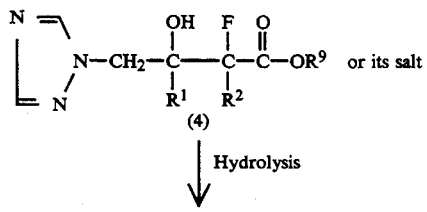

↓ Hydrolysis

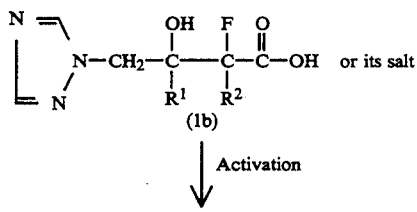

↓ Activation

Reactive derivative of (1b) or its salt

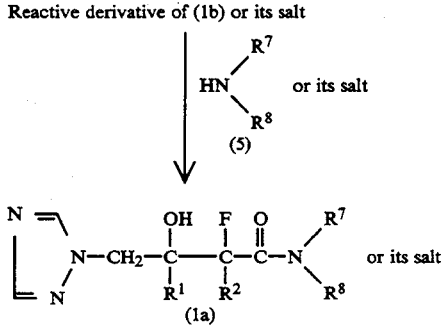

wherein $R^1$, $R^2$, $R^7$ and $R^8$ have the same meanings as defined above.

Process 4

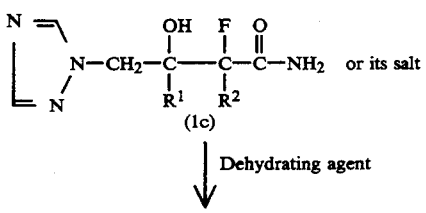

↓ Dehydrating agent

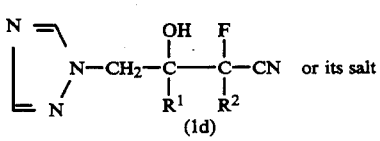

wherein $R^1$ and $R^2$ have the same meanings as defined above.

Process 5

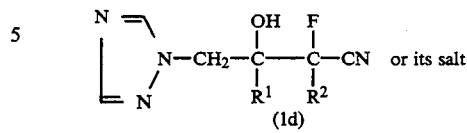

↓ $R^{10}OH$ (6)

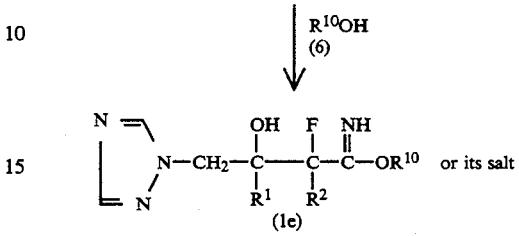

wherein $-OR^{10}$ represents a substituted or unsubstituted alkoxy group which is the same as mentioned in the definition of $R^5$; and $R^1$ and $R^2$ have the same meanings as defined above.

Process 6

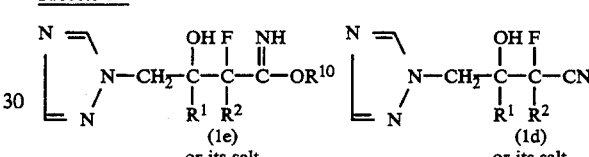

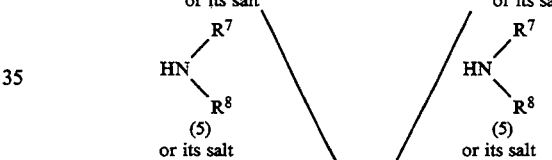

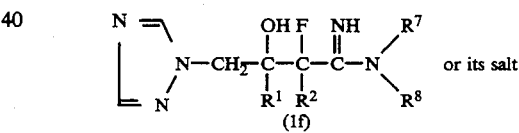

wherein $R^1$, $R^2$, $R^7$, $R^8$ and $-OR^{10}$ have the same meanings as defined above.

Process 7

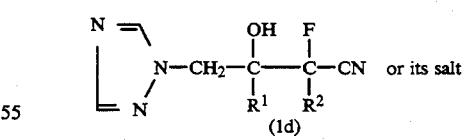

↓ $H_2NOR^6$ or its salt (7)

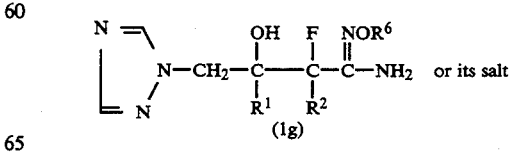

wherein $R^1$, $R^2$ and $R^6$ have the same meanings as defined above.

Process 8

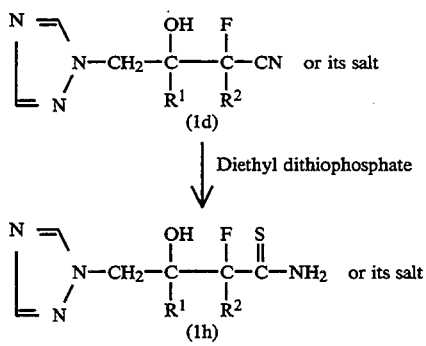

wherein R¹ and R² have the same meanings as defined above.

Next, the processes for producing a novel triazole derivative of the general formula (1) or its salt are described in detail, based on Processes 1-8.

Process 1

The compound of the general formula (1a) or its salt can be produced by reacting a compound of the general formula (2) or (3) with a 1,2,4-triazole or its salt.

The salt of the compound of the general formula (1a) includes the same salts as mentioned as to the compound of the general formula (1).

The salt of 1,2,4-triazole includes, for example, salts with alkali metals such as potassium, sodium and the like; and salts with organic bases such as triethylamine, tributylamine, 1,8-diazabicyclo-[5.4.0]undec-7-ene (DBU) and the like. These salts may also be formed in situ.

The reaction can be conducted in the presence or absence of a solvent. The solvent may be any solvent as long as it does not adversely affect the reaction, and it includes amides such as N,N-dimethylformamide, N,N-dimethylacetamide and the like; alcohols such as methanol, ethanol and the like; ethers such as diethyl ether, tetrahydrofuran and the like; aromatic hydrocarbons such as benzene, toluene and the like; nitriles such as acetonitrile and the like; dimethyl sulfoxide; sulfolane; water; etc. These solvents may be used alone or in admixture of two or more.

The amount of 1,2,4-triazole or its salt used is 1 mole or more per mole of the compound of the general formula (2) or (3).

The reaction is preferably conducted at 20°-150° C. for 0.5-24 hours.

Process 2

The compound of the general formula (1a) or its salt can be produced by reacting a compound of the general formula (4) or its salt with a compound of the general formula (5) or its salt.

The salts of the compounds of the general formulas (4) and (5) include the same salts as mentioned as to the compound of the general formula (1).

The reaction can be conducted in the presence or absence of a solvent. The solvent may be any solvent as long as it does not adversely affect the reaction, and it includes ethers such as diethyl ether, tetrahydrofuran, 1,2-dimethoxyethane and the like; alcohols such as methanol, ethanol and the like; amides such as N,N-dimethylformamide, N,N-dimethylacetamide and the like; dimethyl sulfoxide; water; etc. These solvents may be used alone or in admixture of two or more.

It is also possible to use the compound of the general formula (5) or its salt as a solvent.

The amount of the compound of the general formula (5) or its salt used is 1 mole or more per mole of the compound of the general formula (4) or its salt.

The reaction is preferably conducted at −20° to 200° C. for 0.5-24 hours.

Process 3

The compound of the general formula (1a) or its salt can be produced by subjecting a compound of the general formula (4) or its salt to conventional hydrolysis to convert it to a compound of the general formula (1b) or its salt, activating it by a known method to convert it to a reactive derivative of the compound of the general formula (1b) or its salt, then reacting the reactive derivative with a compound of the general formula (5) or its salt in the same manner as in Process 2.

The salt of the compound of the general formula (1b) includes the same salts as mentioned as to the compound of the general formula (1) and salts with alkali metals such as potassium, sodium and the like.

The reactive derivative of the compound of the general formula (1b) includes acid halides, acid anhydrides, mixed acid anhydrides, active acid amides, active esters, reactive derivatives derived from Vilsmeier reagent, etc.

Process 4

The compound of the general formula (1d) or its salt can be produced by reacting a compound of the general formula (1c) or its salt with a dehydrating agent.

The salts of the compounds of the general formulas (1c) and (1d) include the same salts as mentioned as to the compound of the general formula (1).

The dehydrating agent includes acetic anhydride, benzoyl chloride, trichloroacetyl chloride, thionyl chloride, phosphorus pentoxide, etc.

The reaction can be conducted in the presence or absence of a solvent. The solvent may be any solvent as long as it does not adversely affect the reaction, and includes ethers such as diethyl ether, tetrahydrofuran, dioxane and the like; aromatic hydrocarbons such as benzene, toluene and the like; halogenated hydrocarbons such as methylene chloride, chloroform and the like; pyridine; etc. These solvents may be used alone or in admixture of two or more.

The reaction is preferably conducted at 0°-150° C. for 0.1-24 hours.

Process 5

The compound of the general formula (1e) or its salt can be produced by reacting a compound of the general formula (1d) or its salt with a compound of the general formula (6).

The salt of the compound of the general formula (1e) includes the same salts as mentioned as to the compound of the general formula (1).

The amount of the compound of the general formula (6) used is 1 mole or more per mole of the compound of the general formula (1d) or its salt. It is preferable to use the compound of the general formula (6) as a solvent.

In the reaction, there may be used a solvent which does not adversely affect the reaction. The solvent includes ethers such as diethyl ether, tetrahydrofuran, dioxane and the like; aromatic hydrocarbons such as benzene, toluene and the like; and halogenated hydrocarbons such as methylene chloride, chloroform and the like. These solvents may be used alone or in admixture of two or more.

The reaction is preferably conducted at 0°–100° C. for 0.1–24 hours.

Process 6

The compound of the general formula (1f) or its salt can be produced by reacting a compound of the general formula (1e) or its salt or a compound of the general formula (1d) or its salt with a compound of the general formula (5) or its salt.

The salt of the compound of the general formula (1f) includes the same salts as mentioned as to the compound of the general formula (1).

The reaction can be conducted in the presence or absence of a solvent. The solvent may be any solvent as long as it does not adversely affect the reaction, and includes ethers such as diethyl ether, tetrahydrofuran, dioxane and the like; alcohols such as methanol, ethanol and the like; aromatic hydrocarbons such as benzene, toluene and the like; halogenated hydrocarbons such as methylene chloride, chloroform and the like; etc. These solvents may be used alone or in admixture of two or more.

It is also possible to use the compound of the general formula (5) or its salt as a solvent.

The amount of the compound of the general formula (5) or its salt used is 1 mole or more per mole of the compound of the general formula (1e) or its salt or the compound of the general formula (1d) or its salt.

The reaction is preferably conducted at 0°–150° C. for 0.5–24 hours.

Process 7

The compound of the general formula (1g) or its salt can be produced by reacting a compound of the general formula (1d) or its salt with a compound of the general formula (7) or its salt.

The salts of the compounds of the general formulas (7) and (1g) include the same salts as mentioned as to the compound of the general formula (1).

The reaction can be conducted in the same manner as in Process 6.

A deacidifying agent may be used if necessary. The deacidifying agent includes amines such as triethylamine and the like.

Process 8

The compound of the general formula (1h) or its salt can be produced by reacting a compound of the general formula (1d) or its salt with diethyl dithiophosphate in the presence of water.

The salt of the compound of the general formula (1h) includes the same salts as mentioned as to the compound of the general formula (1).

The amount of diethyl dithiophosphate used is 1 mole or more per mole of the compound of the general formula (1d) or its salt.

The reaction is preferably conducted at 0°–150° C. for 0.5–10 hours.

Next, a description is made on the processes for production of the compound of the general formula (2) or (3) or the compound of the general formula (4) or its salt, which are the starting materials for the production of the compound of the present invention.

The compound of the general formula (2) or (3), or the compound of the general formula (4) or its salt can be produced by, for example, processes A–D described below.

Process A

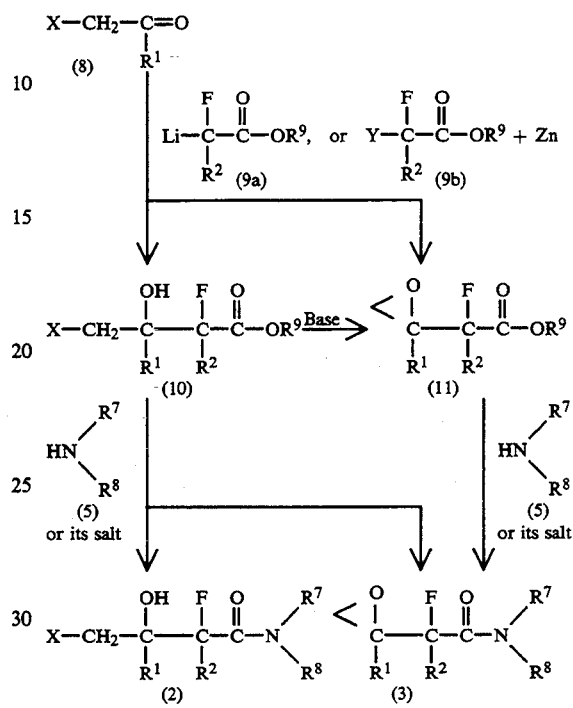

wherein Y represents a halogen atom; and $R^1$, $R^2$, $R^7$, $R^8$, $R^9$ and X have the same meanings as defined above.

Process B

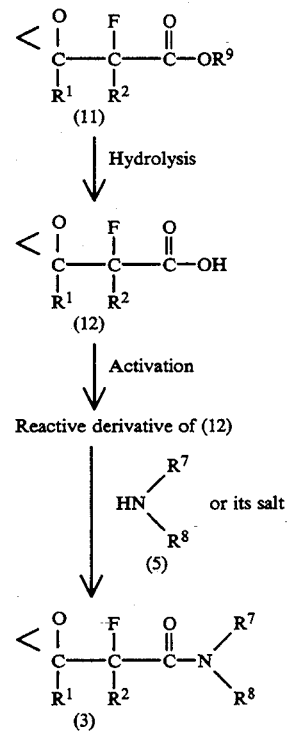

wherein $R^1$, $R^2$, $R^7$, $R^8$ and $R^9$ have the same meanings as defined above.

Process C

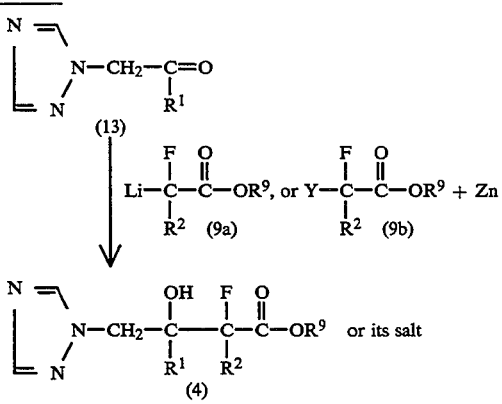

wherein $R^1$, $R^2$, $R^9$ and Y have the same meanings as defined above.

Process D

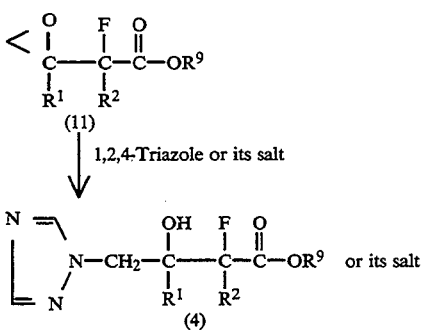

wherein $R^1$, $R^2$ and $R^9$ have the same meanings as defined above.

The processes for the production of the compound of the general formula (2) or (3), or the compound of the general formula (4) or its salt are described in detail below, based on Processes A-D.

Process A

The compound of the general formula (8) can be produced according to known methods or methods similar thereto, for example, the methods described in Org. Synth. I, 109 and II, 480 and Japanese Patent Application Kokai (Laid-Open) No. 58-32868.

Each step of this process is described below.

(i) Production of compound of the general formula (10) or (11)

The compound of the general formula (10) or (11) can be produced by reacting a compound of the general formula (8) with a compound of the general formula (9a) or with a compound of the general formula (9b) and zinc.

This reaction can be conducted according to, for example, the method described in Tetrahedron Lett. 25, 2301 (1984) or Japanese Patent Application Kokai (Laid-Open) No. 59-82376 or 62-249978.

The compound of the general formula (11) can also be produced by reacting the compound of the general formula (10) with a base.

The base includes organic bases such as triethylamine, tributylamine, DBU and the like, and inorganic bases such as potassium carbonate, sodium hydroxide and the like.

(ii) Production of compound of the general formula (2) or (3)

The compound of the general formula (2) or (3) can be produced by reacting the compound of the general formula (10) with a compound of the general formula (5) or its salt.

The compound of the general formula (3) can also be produced by reacting the compound of the general formula (11) with the compound of the general formula (5) or its salt.

These reactions can be conducted in the same manner as in Process 2.

Process B

The compound of the general formula (3) can be produced by subjecting a compound of the general formula (11) to conventional hydrolysis to convert it to a compound of the general formula (12), activating the compound of the general formula (12) by a known method to convert it to a reactive derivative of the compound of the general formula (12), then reacting the reactive derivative with a compound of the general formula (5) or its salt.

This reaction can be conducted in the same manner as in Process 3.

Process C

The compound of the general formula (13) can be produced according to a known method or a method similar thereto, for example, the method described in Japanese Patent Application Kokai (Laid-Open) No. 58-32868 or 59-62575.

The compound of the general formula (4) or its salt can be produced by reacting the compound of the general formula (13) with a compound of the general formula (9a) or with a compound of the general formula (9b) and zinc.

This reaction can be conducted in the same manner as in (i) of Process A.

Process D

The compound of the general formula (4) or its salt can be produced by reacting a compound of the general formula (11) with 1,2,4-triazole or its salt.

This reaction can be conducted in the same manner as in Process 1.

The compound of the general formula (1) or its salt thus obtained can be isolated and purified by conventional methods such as extraction, crystallization, distillation, column chromatography and the like.

The compound of the general formula (1) or its salt can be converted to other desired compounds of the general formula (1) or their salts, by using an appropriate combination of methods known per se such as oxidation, reduction, addition, alkylation, acylation, cyclization, substitution, deprotection, hydrolysis and the like.

When the compound of the present invention is used as a drug or medicine, it is appropriately combined, if necessary, with pharmaceutically acceptable additives such as excipient, carrier, diluent and the like. The resulting mixture is molded into forms such as tablets, capsules, granules, parvules, powder, injection and the like according to a conventional method, and can be administered orally or parenterally. The dose is, in the case of oral administration, preferably about 0.05–200 mg/kg/day of adult body weight. This daily dose may be administered in one or several portions. The dose and number of portions of administration can be appropriately varied depending upon the age, weight and disease condition of patient.

Next, a description is made on the pharmacological actions of the representative compounds of the present invention.

1. Minimum inhibitory concentration (MIC)

MIC was determined in accordance with the method of M.S. Marriott [25th Interscience Conference on Antimicrobial Agents and Chemotherapy, p. 243 (1985)].

*Candida albicans* ON28 was cultured in a sabouraud dextrose agar medium containing 10 g of neopeptone, 20 g of glucose and 15 g of agar per liter, at 30° C. for 1–2 days. The yeast cells were suspended in sterile distilled water. Separately, *Aspergillus fumigatus* IFO8868 was cultured in a potato dextrose agar medium (manufactured by Nissui Pharmaceutical Co., Ltd.) at 30° C. until the conidia were formed abundantly. The formed conidia were suspended in a sterile physiological saline containing 0.1% of Tween 80. Each of the *Candida albicans* suspension and the *Aspergillus fumigatus* suspension was inoculated into a TC broth medium (containing 1.17 g of an yeast carbon base, 0.25 g of ammonium sulfate, 2.0 ml of a 50-fold concentrate of L-glutamic acid-containing MEM amino acid, 20 ml of a 0.5M phosphate buffer of pH 7.5 and 1.33 ml of 7.5% sodium hydrogencarbonate per 100 ml) containing a test compound, so that the final fungal amount became $10^4$ spores/ml. Then, culture was conducted at 37° C. for 3 days. Thereafter, the growth of fungi was examined. The minimum concentration of test compound at which the growth of fungi had been inhibited, was taken as MIC (μg/ml).

The results are shown in Table 1.

TABLE 1

| Example No. | Candida albicans ON28 | Aspergillus fumigatus IFO8868 |
|---|---|---|
| 3 | 0.39 | 12.5 |
| 4 | 0.1 | 50 |
| 5 | ≦0.05 | 12.5 |
| 8 | 0.78 | 25 |
| 11 | 0.2 | 100 |
| 12 | 0.2 | 25 |
| 16 | ≦0.05 | 25 |
| 17 | 0.1 | 12.5 |
| 19 | 0.1 | 50 |
| 20 | ≦0.05 | 100 |
| 21 | ≦0.05 | 100 |
| 22 | ≦0.05 | 12.5 |
| 30 | 0.2 | 12.5 |
| 33 | 0.2 | 50 |
| 35 | ≦0.05 | 25 |
| 39 | 6.25 | 100 |
| 42 | ≦0.05 | 50 |
| 43 | ≦0.05 | 25 |
| 44 | ≦0.05 | 1.56 |
| 45 | ≦0.05 | 50 |
| 51 | 0.1 | 12.5 |
| 56 | 0.39 | 100 |
| 69 | 0.39 | 50 |
| 72 | 0.39 | 50 |
| 73 | 0.39 | 25 |
| 74 | 0.78 | 12.5 |
| 75 | 0.2 | 6.25 |
| 79 | 0.78 | 50 |
| 80 | 0.39 | 12.5 |
| 81 | 0.1 | 3.13 |
| 83 | 0.1 | 25 |
| 85 | 0.1 | 12.5 |
| 88 | 0.2 | 50 |
| 114 | 0.05 | 12.5 |
| 117 | 0.39 | 25 |
| 136 | 0.025 | 12.5 |
| 138 | 0.1 | 12.5 |
| 139 | 0.05 | 12.5 |
| 142 | 0.78 | 100 |
| 143 | 0.2 | 25 |
| 144 | 0.1 | 6.25 |
| 145 | 0.1 | 12.5 |
| 146 | 0.39 | 50 |
| 147 | 0.1 | 6.25 |
| 148 | 0.1 | 3.13 |

2. Therapeutic effect (1) The therapeutic effects of the present compounds, when they were administered orally, were examined using mice infected with *Candida albicans* ON28.

*Candida albicans* ON28 was injected in a proportion of $3.5 \times 10^6$ cells/mouse to a group of 5 ICR strain male mice (weight: 19–21 g) intravenously at the tails, whereby the mice were infected with the fungi. Two hours after the infection, a test compound was orally administered in a proportion of 0.1 mg/mouse to the mice, and their survival was observed for 10 days. The relative therapeutic index of the test compound was determined from the average survival days.

The results are shown in Table 2a, in which the relative therapeutic index of each test compound is a value calculated by taking the average survival days Ketoconazole as 100.

TABLE 2a

| Example No. | Relative therapeutic index |
|---|---|
| 12 | 440 |
| 19 | 625 |
| 30 | 355 |

(2) The therapeutic effects of the present compounds, when they were administered orally, were examined using mice infected with *Aspergillus fumigatus* IFO8868.

*Aspergillus fumigatus* IFO8868 was injected in a proportion of $3.6 \times 10^6$ cells/mouse to a group of 5 ICR strain male mice (weight: 19–21 g) intravenously at the tails, whereby the mice were infected with the fungi. Two hours after the infection, a test compound was orally administered in a proportion of 0.8 mg/mouse to the mice, and their survival was observed for 10 days. The relative therapeutic index of the test compound was determined from the average survival days.

The results are shown in Table 2b, in which the relative therapeutic index of each test compound is a value calculated by taking the average survival days of Ketoconazole as 100.

TABLE 2b

| Example No. | Relative therapeutic index |
|---|---|
| 12 | 150 |
| 19 | 164 |
| 30 | 207 |

(3) The therapeutic effects of the present compounds, when they were administered orally, were examined using mice infected with *Candida albicans* ON28.

*Candida albicans* ON28 was injected in a proportion of $5.7 \times 10^6$ cells/mouse to a group of 10 ICR strain male mice (weight: 19–21 g) intravenously at the tails, whereby the mice were infected with the fungi. Two hours after the infection, a test compound was orally administered in a proportion of 0.1 mg/mouse to the mice, and their survival was observed for 10 days. The relative therapeutic index of the test compound was determined from the average survival days.

The results are shown in Table 2c, in which the relative therapeutic index of each test compound is a value calculated by taking the average survival days Ketoconazole as 100.

TABLE 2c

| Example No. | Relative therapeutic index |
|---|---|
| 10 | 414 |
| 11 | 423 |
| 12 | 445 |
| 19 | 405 |
| 30 | 414 |
| 79 | 405 |
| 80 | 455 |
| 142 | 405 |
| 143 | 450 |
| 145 | 409 |
| 146 | 418 |
| 147 | 414 |

(4) The therapeutic effects of the present compounds, when they were administered orally, were examined using mice infected with *Aspergillus fumigatus* IFO8868.

*Aspergillus fumigatus* IFO8868 was injected in a proportion of $5.8 \times 10^6$ cells/mouse to a group of 10 ICR strain male mice (weight: 19-21 g) intravenously at the tails, whereby the mice were infected with the fungi. Two hours after the infection, and continued once daily for six consecutive days, a test compound was orally administered in a proportion of 0.8 mg/mouse to the mice, and their survival was observed for 10 days. The relative therapeutic index of the test compound was determined from the average survival days.

The results are shown in Table 2d, in which the relative therapeutic index of each test compound is a value calculated by taking the average survival days of Ketoconazole as 100.

TABLE 2d

| Example No. | Relative therapeutic index |
|---|---|
| 10 | 200 |
| 11 | 174 |
| 12 | 237 |
| 19 | 253 |
| 30 | 358 |
| 79 | 400 |
| 80 | 416 |
| 142 | 216 |
| 143 | 242 |
| 145 | 353 |
| 146 | 500 |
| 147 | 526 |

3. Acute toxicity

Each of the compounds of Examples 10, 12, 19, 79, 142 and 146 was administered to a group of 5 ICR strain male mice (weight: 29-31 g) intravenously at the tails, and the acute toxicity of each compound was examined.

Each compound was administered in the form of a 50% solution in polyethylene glycol 300.

As a result, the compounds of Example Nos. 12 and 19 gave no dead case when the dose was up to 100 mg/kg, and the compounds of Example Nos. 10, 79, 142 and 146 gave no dead case when the dose was up to 200 mg/kg.

As is clear from the above test results, the present compound exhibits very high pharmacological effects and is highly safe.

The present invention is hereinafter described in more detail referring to Reference Examples and Examples. However, the present invention is not restricted to the Examples.

The carrier used in column chromatography was Silica Gel 60 (manufactured by Merck Co.).

The mixing ratio concerning eluant is by volume in all cases.

In the remarks column of Tables, A and B refer to one of diastereomers and the other, respectively; C refers to a mixture of diastereomers; D refers to a dihydrochloride; E refers to a p-toluenesulfonic acid salt; F refers to an optically active compound; G refers to a monohydrochloride; and H refers to a dioxane adduct.

REFERENCE EXAMPLE 1

In 20 ml of dried tetrahydrofuran was suspended 0.97 g of zinc. To the suspension was dropwise added 3.0 g of ethyl bromodifluoroacetate under reflux. Then, 10 ml of a solution of 2.2 g of 2,2',4'-trichloroacetophenone dissolved in dried tetrahydrofuran was dropwise added under reflux. The resulting mixture was refluxed for 10 minutes. The insolubles were removed by filtration. The solvent was removed by distillation under reduced pressure. To the residue obtained were added 20 ml of ethyl acetate and 20 ml of water. The resulting solution was adjusted to pH 1.0 with 6N hydrochloric acid. The organic layer was separated, washed with a saturated aqueous sodium chloride solution, and then dried over anhydrous magnesium sulfate. The solvent was removed by distillation under reduced pressure. The residue thus obtained was purified by a column chromatography (eluant: n-hexane/toluene=1/2) to obtain 1.8 g of oily ethyl 4-chloro-3-(2,4-dichlorophenyl)-2,2-difluoro-3-hydroxybutyrate.

IR (neat) cm$^{-1}$: 3500, 2975, 1755, 1580, 1550

REFERENCE EXAMPLES 2-6

The compounds shown in Table 3 were obtained in the same manner as in Reference Example 1.

In Table 3, $R^1$, $R^2$ and X are those of the following formula:

TABLE 3

$$X-CH_2-\underset{\underset{R^1}{|}}{\overset{\overset{OH}{|}}{C}}-\underset{\underset{R^2}{|}}{\overset{\overset{F}{|}}{C}}-\overset{\overset{O}{\|}}{C}OC_2H_5$$

| Reference Example No. | $R^1$ | $R^2$ | X | IR (neat) cm$^{-1}$ | Remarks |
|---|---|---|---|---|---|
| 2 | 2-Cl-C₆H₄ | F | Br | 3530, 1760, 1310, 1140 | |
| 3 | thiazolyl | F | Br | 3450, 1755, 1370, 1305 | |
| 4 | 2,4-F₂-C₆H₃ | F | Cl | 3500, 1755, 1610, 1590 | |

TABLE 3-continued $$X-CH_2-\underset{\underset{R^1}{|}}{\overset{\overset{OH}{|}}{C}}-\underset{\underset{R^2}{|}}{\overset{\overset{F}{|}}{C}}-\overset{\overset{O}{\|}}{C}OC_2H_5$$

| Reference Example No. | $R^1$ | $R^2$ | X | IR (neat) cm$^{-1}$ | Remarks |
|---|---|---|---|---|---|
| 5 | 2,4-F₂-C₆H₃ | H | Cl | 3450, 1750, 1605, 1490 | C |
| 6 | 2-F-C₆H₄ | F | Cl | (KBr) 3410, 1745, 1490, 1135 | |

REFERENCE EXAMPLE 7

To 40 ml of a solution of lithium diisopropylamide in dried diethyl ether prepared from 4.3 g of diisopropylamine and 26.0 ml of a 1.64N n-hexane solution of n-butyllithium was dropwise added 10 ml of a dried diethyl ether solution containing 5.1 g of ethyl 2-fluoropropionate at −70° to −60° C. The mixture was stirred at the same temperature for 15 minutes. Thereto was dropwise added 60 ml of a dried diethyl ether solution containing 6.2 g of 2-chloro-2',4'-difluoroacetophenone at −70° to −60° C. Then, the temperature of the mixture was elevated to 20° C. in 5 hours. The reaction mixture obtained was introduced into a mixed solvent consisting of 100 ml of ethyl acetate and 50 ml of water. The resulting solution was adjusted to pH 2.0 with 6N hydrochloric acid. The organic layer was separated, washed with a saturated aqueous sodium chloride solution, and then dried over anhydrous magnesium sulfate. The solvent was removed by distillation under reduced pressure. The residue thus obtained was purified by a column chromatography (eluant: n-hexane/toluene=2/1) to obtain 3.9 g of oily ethyl 3-(2,4-difluorophenyl)-3,4-epoxy-2-fluoro-2-methylbutyrate (a mixture of diastereomers).

IR (neat) cm$^{-1}$: 2985, 1760, 1740, 1505, 1140

REFERENCE EXAMPLE 8

In the column chromatography of Reference Example 7, elution was further conducted with an eluant (n-hexane/toluene=1/1) to obtain 3 g of oily ethyl 4-chloro-3-(2,4-difluorophenyl)-2-fluoro-3-hydroxy-2-methylbutyrate (a mixture of diastereomers).

IR (neat) cm$^{-1}$: 3490, 1745, 1615, 1300, 1145

REFERENCE EXAMPLE 9

In 150 ml of methylene chloride was dissolved 15.7 g of ethyl 4-chloro-3-(2,4-difluorophenyl)-2,2-difluoro-3-hydroxybutyrate. To the solution was dropwise added 8.4 g of 1,8-diazabicyclo[5.4.0]undec-7-ene at 5°–10° C. The mixture was subjected to reaction at the same temperature for 2 hours. The resulting reaction mixture was introduced into 150 ml of water and adjusted to pH 1.0 with 6N hydrochloric acid. The organic layer was separated, washed with a saturated aqueous sodium chloride solution, and then dried over anhydrous magnesium sulfate. The solvent was removed by distillation under reduced pressure. The residue thus obtained was purified by a column chromatography (eluant: n-hexane/toluene=2/1) to obtain 11.1 g of oily ethyl 3-(2,4-difluorophenyl)-3,4-epoxy-2,2-difluorobutyrate.

IR (neat) cm$^{-1}$: 1770, 1620, 1510, 1145

REFERENCE EXAMPLE 10

Ethyl 3-(2,4-difluorophenyl)-3,4-epoxy-2-fluorobutyrate (a mixture of diastereomers) was obtained from ethyl 4-chloro-3-(2,4-difluorophenyl)-2-fluoro-3-hydroxybutyrate (a mixture of diastereomers) in the same manner as in Reference Example 9.

IR (neat) cm$^{-1}$: 2980, 1760, 1615, 1505

REFERENCE EXAMPLE 11

In 17 ml of ethanol was dissolved 1.7 g of ethyl 4-chloro-3-(2,4-dichlorophenyl)-2,2-difluoro-3-hydroxybutyrate. To the resulting solution was added 16.3 ml of a 3N ammonia-ethanol solution. The solution was subjected to reaction at 25°–30° C. for 24 hours. Then, the solvent was removed by distillation under reduced pressure. To the residue obtained were added 20 ml of ethyl acetate and 20 ml of water. The resulting mixture was adjusted to pH 1.0 with 6N hydrochloric acid. The organic layer was separated, washed with a saturated aqueous sodium chloride solution, and then dried over anhydrous magnesium sulfate. The solvent was removed by distillation under reduced pressure. The residue thus obtained was purified by a column chromatography (eluant: chloroform) to obtain 0.88 g of 3-(2,4-dichlorophenyl)-3,4-epoxy-2,2-difluorobutanamide.

Melting point: 100.0°–101.0° C.

IR (KBr) cm$^{-1}$: 3460, 3280, 3190, 1690, 1610

REFERENCE EXAMPLES 12–14

The compounds shown in Table 4 were obtained in the same manner as in Reference Example 11. In Table 4, $R^1$, $R^2$, $R^7$ and $R^8$ are those of the following formula:

TABLE 4

$$\triangleleft\underset{\underset{R^1}{|}}{\overset{\overset{O}{|}}{C}}-\underset{\underset{R^2}{|}}{\overset{\overset{F}{|}}{C}}-\overset{\overset{O}{\|}}{C}-N\underset{R^8}{\overset{R^7}{<}}$$

| Reference Example No. | $R^1$ | $R^2$ | $R^7$ | $R^8$ | IR (KBr) cm$^{-1}$ | Remarks |
|---|---|---|---|---|---|---|
| 12 | 2-Cl-C₆H₄ | F | H | H | 3470, 1705, 1590 | |
| 13 | 2-Cl-C₆H₄ | F | cyclopropyl | H | 3270, 1675, 1535 | |

TABLE 4-continued $$\begin{array}{c} O \quad F \quad O \quad R^7 \\ < \begin{array}{c} | \quad | \quad \| \quad / \\ C-C-C-N \\ | \quad | \quad \quad \backslash \\ R^1 \quad R^2 \quad \quad R^8 \end{array} \end{array}$$

| Reference Example No. | $R^1$ | $R^2$ | $R^7$ | $R^8$ | IR (KBr) cm$^{-1}$ | Remarks |
|---|---|---|---|---|---|---|
| 14 | 4-fluorophenyl (with F substituent) | F | H | H | 3400, 1660, 1495 | C |

REFERENCE EXAMPLE 15

Diastereomers A and B of 3-(2,4-difluorophenyl)-3,4-epoxy-2-fluoro-2-methylbutanamide were obtained from ethyl 3-(2,4-difluorophenyl)-3,4-epoxy-2-fluoro-2-methylbutyrate (a mixture of diastereomers) in the same manner as in Reference Example 11.

IR (KBr) cm$^{-1}$:
3455, 1665, 1505, 1265 (diastereomer A)
3385, 1700, 1505, 1150 (diastereomer B)

REFERENCE EXAMPLE 16

4-Bromo-2,2-difluoro-3-hydroxy-3-(thiazol-2-yl)butanamide was obtained from ethyl 4-bromo-2,2-difluoro-3-hydroxy-3-(thiazol-2-yl)butyrate in the same manner as in Reference Example 11.

IR (neat) cm$^{-1}$: 3330, 1700, 1405, 1120

REFERENCE EXAMPLE 17

N-cyclopropyl-4-chloro-2,2-difluoro-3-(2-fluorophenyl)-3-hydroxybutanamide was obtained from ethyl 4-chloro-2,2-difluoro-3-(2-fluorophenyl)-3-hydroxybutyrate and cyclopropylamine in the same manner as in Reference Example 11.

IR (KBr) cm$^{-1}$: 3355, 1675, 1540, 1485

REFERENCE EXAMPLE 18

In 11 ml of ethanol was dissolved 1.1 g of ethyl 3-(2,4-difluorophenyl)-3,4-epoxy-2,2-difluorobutyrate. To the resulting solution was dropwise added 4.7 ml of a 1N aqueous sodium hydroxide solution at 5°–10° C. The solution was subjected to reaction at the same temperature for 10 minutes. The reaction mixture was introduced into a mixed solvent consisting of 50 ml of ethyl acetate and 50 ml of water. The resulting solution was adjusted to pH 1.0 with 6N hydrochloric acid. The organic layer was separated, washed with a saturated aqueous sodium chloride solution, and then dried over anhydrous magnesium sulfate. The solvent was removed by distillation under reduced pressure to obtain 0.99 g of oily 3-(2,4-difluorophenyl)-3,4-epoxy-2,2-difluorobutyric acid.

REFERENCE EXAMPLE 19

(1) In 18 ml of dioxane were dissolved 0.9 g of 3-(2,4-difluorophenyl)-3,4-epoxy-2,2-difluorobutyric acid and 0.41 g of N-hydroxysuccinimide. To the resulting solution was added 0.74 g of N,N'-dicyclohexylcarbodiimide. The solution was subjected to reaction at room temperature for 1 hour. The insolubles were removed by filtration.

(2) In a mixed solvent consisting of 14 ml of dioxane and 29 ml of a 1N aqueous sodium hydroxide solution was suspended 1.4 g of 1-(4-chlorophenyl)cyclopropanecarboxamide [this compound can be obtained from 1-(4-chlorophenyl)cyclopropanecarboxylic acid produced according to the method described in Chem. Ber., 119, 3694 (1986)]. To the suspension was dropwise added 4.4 g of a 12% aqueous sodium hypochlorite solution at 5°–10° C. The suspension was subjected to reaction at 20°–25° C. for 1 hour. The reaction mixture was introduced into a mixed solvent consisting of 50 ml of ethyl acetate and 50 ml of water. The organic layer was separated, washed with a saturated aqueous sodium chloride solution, and then dried over anhydrous magnesium sulfate. To the thus treated organic layer was added the dioxane solution obtained in (1) above at 20°–25° C. The resulting mixture was subjected to reaction at the same temperature for 2 hours. The insolubles were removed by filtration. The solvent was removed by distillation under reduced pressure. To the residue obtained were added 50 ml of ethyl acetate and 50 ml of water. The organic layer was separated, washed with a saturated aqueous sodium chloride solution, and then dried over anhydrous magnesium sulfate. The solvent was removed by distillation under reduced pressure. The residue obtained was purified by a column chromatography (eluant: n-hexane/ethyl acetate =15/1) to obtain 0.37 g of N-[1-(4-chlorophenyl)cyclopropyl]-3-(2,4-difluorophenyl)-3,4-epoxy-2,2-difluorobutanamide.

IR (neat) cm$^{-1}$: 3325, 1705, 1620, 1600, 1510

REFERENCE EXAMPLE 20

N-(1-methylcyclopropyl)-3-(2,4-difluorophenyl)-3,4-epoxy-2,2-difluorobutanamide was obtained in the same manner as in Reference Example 19.

REFERENCE EXAMPLE 21

Ethyl 3-(2,4-difluorophenyl)-2,2-difluoro-3-hydroxy-4-(1H-1,2,4-triazol-1-yl)butyrate was obtained in the same manner as in Reference Example 1, using zinc, ethyl bromodifluoroacetate and 1-(2,4-difluorophenyl)-2-(1H-1,2,4-triazol-1-yl)ethan-1-one.

Melting point: 106.5°–108.0° C.
IR (KBr) cm$^{-1}$: 3445, 3110, 1765, 1615, 1505

REFERENCE EXAMPLES 22–23

The compounds shown in Table 5 were obtained in the same manner as in Reference Example 21. In Table 5, $R^1$ and $R^2$ are those of the following formula:

TABLE 5

$$\begin{array}{c} N= \\ \big[ \quad \quad \quad \quad OH \quad F \quad O \\ \quad \quad \quad | \quad \quad | \quad \| \\ \quad \quad N-CH_2-C-C-COC_2H_5 \\ / \quad \quad \quad | \quad | \\ N \quad \quad \quad R^1 \quad R^2 \end{array}$$

| Reference Example No. | $R^1$ | $R^2$ | IR (KBr) cm$^{-1}$ |
|---|---|---|---|
| 22 | 4-fluorophenyl (Cl substituent) | F | 3450, 1770, 1605 |

TABLE 5-continued

Structure:
N≡N-N-CH₂-C(OH)(R¹)-C(F)(R²)-COC₂H₅ with carbonyl O

| Reference Example No. | R¹ | R² | IR (KBr) cm⁻¹ |
|---|---|---|---|
| 23 | (4-chloro-2-pyridyl group: N in ring, Cl substituent) | F | — |

REFERENCE EXAMPLE 24

Ethyl 2-benzyl-3-(2,4-difluorophenyl)-2-fluoro-3-hydroxy-4-(1H-1,2,4-triazol-1-yl)butyrate (a mixture of diastereomers) was obtained in the same manner as in Reference Example 7, using ethyl 2-fluoro-3-phenylpropionate and 1-(2,4-difluorophenyl)-2-(1H-1,2,4-triazol-1-yl)ethan-1-one.

IR (neat) cm⁻¹: 3385, 1740, 1500, 1275

REFERENCE EXAMPLE 25

Ethyl 2-fluoropropionate and 1-(2,4-difluorophenyl)-2-(1H-1,2,4-triazol-1-yl)ethan-1-one were treated in the same manner as in Reference Example 7, and the residue thus obtained was purified by a column chromatography (eluant: ethyl acetate/toluene=1/4) to obtain ethyl 3-(2,4-difluorophenyl)-2-fluoro-3-hydroxy-2-methyl-4-(1H-1,2,4-triazol-1-yl)butyrate (one of the diastereomers).

IR (KBr) cm⁻¹: 3460, 1740, 1615, 1500

REFERENCE EXAMPLE 26

A mixture of 2.4 g of ethyl 3-(2,4-difluorophenyl)-3,4-epoxy-2-fluorobutyrate (a mixture of diastereomers) and 6.4 g of 1,2,4-triazole was subjected to reaction at 90°-100° C. for 8 hours. To the reaction mixture were then added 10 ml of ethyl acetate and 5 ml of water. The organic layer was separated, washed with a saturated aqueous sodium chloride solution, and then dried over anhydrous magnesium sulfate. The solvent was removed by distillation under reduced pressure. The residue obtained was purified by a column chromatography (eluant: chloroform/methanol=20/1) to obtain 650 mg of ethyl 3-(2,4-difluorophenyl)-2-fluoro-3-hydroxy-4-(1H-1,2,4-triazol-1-yl)butyrate (one of the diastereomers).

IR (KBr) cm⁻¹: 3140, 1760, 1620, 1210, 1100

Elution was further continued to obtain 170 mg of the other of the diastereomers.

IR (KBr) cm⁻¹: 3135, 1755, 1505, 1220, 1130

REFERENCE EXAMPLES 27–38

The compounds shown in Table 6 were obtained in the same manner as in Reference Example 1.

In Table 6, R¹ and X are those of the following formula:

TABLE 6

Structure: X-CH₂-C(OH)(R¹)-C(F)-COC₂H₅ with carbonyl O

| Reference Example No. | R¹ | X | IR (neat) cm⁻¹ |
|---|---|---|---|
| 27 | phenyl | Cl | 3510, 1760, 1315, 1095 |
| 28 | 2,4-difluorophenyl | Cl | 3615, 1765, 1470, 1110 |
| 29 | 2,4-dichlorophenyl | Cl | — |
| 30 | 2-fluoro-4-chlorophenyl | Cl | 3495, 1760, 1315, 1080 |
| 31 | 2-fluoro-4-chlorophenyl (isomer) | Cl | 3540, 1765, 1450, 1150 |
| 32 | 2,4,5-trifluorophenyl | Cl | 3620, 1765, 1600, 1125 |
| 33 | 2,4,5-trifluorophenyl (isomer) | Cl | 3460, 1760, 1515, 1420 |
| 34 | 2,3,4-trifluorophenyl | Cl | 3490, 1760, 1515, 1475 |
| 35 | 2-chloro-4,6-difluorophenyl | Cl | 3420, 1750, 1500, 1180 |

TABLE 6-continued $$X-CH_2-\underset{\underset{R^1}{|}}{\overset{\overset{OH}{|}}{C}}-\underset{\underset{F}{|}}{\overset{\overset{F}{|}}{C}}-\overset{\overset{O}{\|}}{C}OC_2H_5$$

| Reference Example No. | $R^1$ | X | IR (neat) cm$^{-1}$ |
|---|---|---|---|
| 36 | 2-fluoro-4-(trifluoromethyl)phenyl | Cl | 3495, 1765, 1425, 1335 |
| 37 | 4-chloro-2-fluoro-5-methylphenyl | Cl | 3505, 1760, 1485, 1315 |
| 38 | 4-(trifluoromethoxy)phenyl | Cl | 3505, 1760, 1510, 1165 |

REFERENCE EXAMPLE 39

Ethyl 3,4-epoxy-2,2-difluoro-3-(2-methoxyphenyl)-butyrate was obtained from 2-bromo-2'-methoxyacetophenone in the same manner as in Reference Example 1.

IR (neat) cm$^{-1}$: 1770, 1605, 1310, 1020

REFERENCE EXAMPLES 40–52

The compounds shown in Table 7 were obtained in the same manner as in Reference Example 21.

In Table 7, $R^1$ is that of the following formula:

TABLE 7

$$\underset{\underset{N}{\Vert}}{\overset{N \rightleftharpoons}{\diagdown}}N-CH_2-\underset{\underset{R^1}{|}}{\overset{\overset{OH}{|}}{C}}-\underset{\underset{F}{|}}{\overset{\overset{F}{|}}{C}}-\overset{\overset{O}{\|}}{C}OC_2H_5$$

| Reference Example No. | $R^1$ | IR (KBr) cm$^{-1}$ |
|---|---|---|
| 40 | 4-fluorophenyl | 3130, 1765, 1520, 1140 |
| 41 | 4-chlorophenyl | 3070, 1765, 1515, 1315 |
| 42 | 3-chlorophenyl | 3170, 1770, 1305, 1140 |
| 43 | 2,4-difluorophenyl | 3120, 1755, 1495, 1315 |
| 44 | 4-(trifluoromethyl)phenyl | 3130, 1765, 1330, 1130 |
| 45 | 4-chloro-2-methylphenyl | (neat) 3135, 1765, 1315, 1135 |
| 46 | 2-chloro-4-methylphenyl | (neat) 3355, 1770, 1605, 1315 |
| 47 | 4-methylphenyl | (neat) 3135, 1765, 1310, 1100 |
| 48 | 2-methylphenyl | (neat) 3130, 1760, 1510, 1140 |
| 49 | 4-methoxyphenyl | (neat) 3135, 1765, 1515, 1100 |
| 50 | 4-cyanophenyl | (neat) 3405, 1765, 1310, 1100 |
| 51 | 4-nitrophenyl | (neat) 3125, 1765, 1530, 1350 |
| 52 | 1-naphthyl | (neat) 1765, 1515 |

EXAMPLE 1

In 8 ml of N,N-dimethylformamide was dissolved 0.8 g of 3-(2,4-dichlorophenyl)-3,4-epoxy-2,2-difluorobutanamide. To the resulting solution were added 0.59 g of anhydrous potassium carbonate and 0.29 g of 1,2,4-triazole. The mixture was subjected to reaction at 80°–90° C. for 1 hour. The solvent was removed by distillation under reduced pressure. To the residue obtained were added 10 ml of ethyl acetate and 10 ml of water. The mixture was adjusted to pH 1.0 with 2N hydrochloric acid. The organic layer was separated, washed with a saturated aqueous sodium chloride solution, and then dried over anhydrous magnesium sulfate. Thereafter, the solvent was removed by distillation under reduced pressure. The residue thus obtained was purified by a column chromatography (eluant: chloroform/methanol=100/1) to obtain 0.40 g of 3-(2,4-dichlorophenyl)-2,2-difluoro-3-hydroxy-4-(1H-1,2,4-triazol-1-yl)butanamide.
Melting point: 194.0°–195.5° C.
IR (KBr) cm$^{-1}$: 3310, 3110, 1700, 1580, 1500

EXAMPLES 2–6

The compounds shown in Table 8 were obtained in the same manner as in Example 1. In Table 8, $R^1$, $R^2$, $R^7$ and $R^8$ are those of the following formula:

EXAMPLE 7

2,2-Difluoro-3-hydroxy-3-(thiazol-2-yl)-4-(1H-1,2,4-triazol-1-yl)butanamide was obtained from 4-bromo-2,2-difluoro-3-hydroxy-3-(thiazol-2-yl)butanamide in the same manner as in Example 1.
Melting point: 173.0°–175.0° C.
IR (KBr) cm$^{-1}$: 3260, 1715, 1515, 1180, 1105

EXAMPLE 8

N-cyclopropyl-2,2-difluoro-3-(2-fluorophenyl)-3-hydroxy-4-(1H-1,2,4-triazol-1-yl)butanamide was obtained from N-cyclopropyl-4-chloro-2,2-difluoro-3-(2-fluorophenyl)-3-hydroxybutanamide in the same manner as in Example 1.
Melting point: 134.5°–135.0° C.
IR (KBr) cm$^{-1}$: 3395, 3160, 1695, 1520

EXAMPLE 9

3-(2,4-Difluorophenyl)-2-fluoro-3-hydroxy-4-(1H-1,2,4-triazol-1-yl)butanamide (one of the diastereomers) was obtained from 3-(2,4-difluorophenyl)-3,4-epoxy-2-fluorobutanamide (a mixture of diastereomers) in the same manner as in Reference Example 26.
Melting point: 185.5°–188.5° C.
IR (KBr) cm$^{-1}$: 3230, 1690, 1615, 1500, 1140

TABLE 8

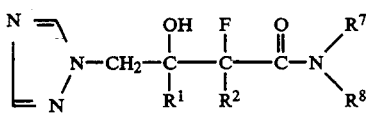

| Example No. | $R^1$ | $R^2$ | $R^7$ | $R^8$ | Melting Point (°C.) | IR (KBr) cm$^{-1}$ | Remarks |
|---|---|---|---|---|---|---|---|
| 2 | Cl-phenyl | F | H | H | Amorphous | 3500, 1710, 1505, 1420 | |
| 3 | Cl-phenyl | F | cyclopropyl | H | 112.0–114.0 | 3275, 1670, 1505, 1425 | |
| 4 | F,F-phenyl | F | 1-methylcyclopropyl | H | 124.5–125.5 | 3325, 1675, 1615, 1540 | |
| 5 | F,F-phenyl | F | 1-(4-chlorophenyl)cyclopropyl | H | Amorphous | 3410, 1700, 1615, 1500 | |
| 6 | F,F-phenyl | —CH$_3$ | H | H | 120.5–121.0<br>134.0–136.0 | 3490, 1675, 1500, 1420<br>3445, 1675, 1500, 1275 | A<br>B |

EXAMPLE 10

In 30 ml of ethanol was dissolved 3.0 g of ethyl 3-(2,4-difluorophenyl)-2,2-difluoro-3-hydroxy-4-(1H-1,2,4-triazol-1-yl)butyrate. To the resulting solution was added 6 ml of concentrated aqueous ammonia. The resulting mixture was subjected to reaction at 20°-25° C. for 5 hours. Then, the solvent was removed by distillation under reduced pressure. The residue obtained was purified by a column chromatography (eluant: chloroform/methanol=20/1) to obtain 2.1 g of 3-(2,4-difluorophenyl)-2,2-difluoro-3-hydroxy-4-(1H-1,2,4-triazol-1-yl)butanamide.

Melting point: 164.5°-165.0° C.
IR (KBr) cm$^{-1}$: 3300, 1690, 1610, 1435, 1270

EXAMPLES 11-38

The compounds shown in Table 9 were obtained in the same manner as in Example 10. In Table 9, $R^1$, $R^2$, $R^7$ and $R^8$ are those of the following formula:

TABLE 9

| Example No. | $R^1$ | $R^2$ | $R^7$ | $R^8$ | Melting Point (°C.) | IR (KBr) cm$^{-1}$ | Remarks |
|---|---|---|---|---|---|---|---|
| 11 | 2,4-difluorophenyl | F | H | —CH$_3$ | 165.5–166.5 | 3350, 1685, 1495, 1275 | |
| 12 | 2,4-difluorophenyl | F | H | —CH$_2$CH$_3$ | 125.0–125.5 | 3330, 1690, 1505, 1105 | |
| 13 | 2,4-difluorophenyl | F | H | —CH$_2$CF$_3$ | 129.0–129.5 | 3345, 1710, 1620, 1540 | |
| 14 | 2,4-difluorophenyl | F | H | —CH$_2$CH$_2$OH | 101.0–103.0 | 3300, 1680, 1505, 1270 | |
| 15 | 2,4-difluorophenyl | F | H | —CH$_2$CH$_2$N(CH$_3$)$_2$ | 247.0–249.0 (decomp.) | 3265, 2695, 1705, 1545 | D |
| 16 | 2,4-difluorophenyl | F | H | —CH$_2$CH$_2$CH$_3$ | 100.5–101.5 | 3330, 1695, 1615, 1540 | |
| 17 | 2,4-difluorophenyl | F | H | —CH$_2$CH=CH$_2$ | 123.5–124.0 | 3330, 1685, 1540, 1420 | |
| 18 | 2,4-difluorophenyl | F | H | —CH$_2$C≡CH | 92.0–94.0 | 3305, 1695, 1615, 1505 | |

TABLE 9-continued

Structure:
$$\text{pyrazolyl-N-CH}_2-\underset{R^1}{\underset{|}{C}}(OH)-\underset{R^2}{\underset{|}{C}}(F)-C(=O)-N(R^7)(R^8)$$

| Example No. | R¹ | R² | R⁷ | R⁸ | Melting Point (°C.) | IR (KBr) cm⁻¹ | Remarks |
|---|---|---|---|---|---|---|---|
| 19 | 2,4-difluorophenyl | F | H | cyclopropyl | 156.0–157.0 | 3315, 1675, 1505, 1275 | |
| 20 | 2,4-difluorophenyl | F | H | cyclopentyl | 132.5–133.0 | 3325, 1685, 1505, 1425 | |
| 21 | 2,4-difluorophenyl | F | H | cyclohexyl | 145.5–146.5 | 3230, 1675, 1500, 1135 | |
| 22 | 2,4-difluorophenyl | F | H | —CH₂—C₆H₄—Cl | 107.0–108.0 | 3360, 1700, 1500, 1425 | |
| 23 | 2,4-difluorophenyl | F | H | —CH(CH₃)COOC₂H₅ | Oily | (neat) 3355, 1740, 1700, 1615 | |
| 24 | 2,4-difluorophenyl | F | | —(CH₂)₄— | 144.0–144.5 | 3070, 1640, 1495, 1440 | |
| 25 | 2,4-difluorophenyl | F | | —(CH₂)₂N(CH₃)(CH₂)₂— | Amorphous | (neat) 3125, 1655, 1450, 1275 | |
| 26 | 2,4-difluorophenyl | F | H | —NH₂ | 194.0–195.0 | 3150, 1690, 1625, 1610 | |
| 27 | 2,4-difluorophenyl | F | H | —OH | 175.0–176.0 (decomp.) | 3150, 1670, 1610, 1590 | |
| 28 | 2,4-difluorophenyl | H | H | cyclopropyl | 160.5–161.5 / 90.5–91.0 | 3240, 1675, 1505, 1275 / 3290, 1650, 1505, 1275 | A / B |

TABLE 9-continued

Structure:

$$\underset{N}{\overset{N}{\underset{\|}{\bigvee}}}N-CH_2-\underset{R^1}{\overset{OH}{\underset{|}{C}}}-\underset{R^2}{\overset{F}{\underset{|}{C}}}-\overset{O}{\underset{\|}{C}}-N\underset{R^8}{\overset{R^7}{\diagup}}$$

| Example No. | $R^1$ | $R^2$ | $R^7$ | $R^8$ | Melting Point (°C.) | IR (KBr) cm$^{-1}$ | Remarks |
|---|---|---|---|---|---|---|---|
| 29 | 2,4-difluorophenyl | —CH$_3$ | H | cyclopropyl | 165.0–166.0 | 3320, 1640, 1550, 1505 | A |
| 30 | 2-chloro-4-fluorophenyl | F | H | cyclopropyl | 109.5–110.5 | 3270, 1685, 1605, 1510 | |
| 31 | 6-chloropyridin-3-yl | F | H | H | — | 3350, 1720, 1365, 1110 | |
| 32 | 2,4-difluorophenyl | F | H | —CH$_2$CH$_2$OCH$_3$ | 83.0–84.0 | 3335, 1695, 1545, 1500 | |
| 33 | 2,4-difluorophenyl | F | H | —CH(CH$_3$)$_2$ | 122.5–123.0 | 3345, 1685, 1620, 1505 | |
| 34 | 2,4-difluorophenyl | F | H | —CH$_2$CH$_2$CN | 123.0–124.0 | 3330, 2265, 1705, 1515 | |
| 35 | 2,4-difluorophenyl | F | H | —CH$_2$CH(CH$_3$)$_2$ | 101.0–101.5 | 3240, 1680, 1505, 1110 | |
| 36 | 2,4-difluorophenyl | F | H | —CH$_2$CH$_2$SH | 105.5–107.0 | 3315, 1685, 1505, 1135 | |
| 37 | 2,4-difluorophenyl | F | H | —CH$_2$CH$_2$SCH$_3$ | — | 3345, 1690, 1505, 1105 | |
| 38 | 2,4-difluorophenyl | F | H | —CH$_2$CH$_2$CH$_2$CN | 135.0–135.5 | 3480, 2245, 1680, 1505 | |

EXAMPLE 39

In 1 ml of ethanol was dissolved 100 mg of ethyl 3-(2,4-difluorophenyl)-2,2-difluoro-3-hydroxy-4-(1H-1,2,4-triazol-1-yl)butyrate. To the resulting solution was added 330 mg of 2,6-dimethylmorpholine. The resulting mixture was subjected to reaction for 2 hours under reflux. Then, the reaction mixture was introduced into a mixed solvent consisting of 20 ml of ethyl acetate and 10 ml of water. The resulting solution was adjusted to pH 2.0 with 6N hydrochloric acid. The organic layer was separated, washed with a saturated aqueous sodium chloride solution, and then dried over anhydrous magnesium sulfate. Thereafter, the solvent was removed by distillation under reduced pressure. The residue obtained was purified by a column chromatography (eluant: chloroform) to obtain 10 mg of 4-[3-(2,4-difluorophenyl)-2,2-difluoro-3-hydroxy-4-(1H-1,2,4-triazol-1-yl)butanoyl]-2,6-dimethylmorpholine.

IR (KBr) cm$^{-1}$: 3445, 1660, 1505, 1275, 1085

EXAMPLES 40–41

The compounds shown in Table 10 were obtained in the same manner as in Example 39. In Table 10, $R^1$, $R^2$, $R^7$ and $R^8$ are those of the following formula:

EXAMPLE 42

A mixture of 100 mg of ethyl 3-(2,4-difluorophenyl)-2,2-difluoro-3-hydroxy-4-(1H-1,2,4-triazol-1-yl)butyrate and 370 mg of 4-chloroaniline was subjected to reaction at 150°–160° C. for 5 hours. The reaction mixture was cooled to room temperature. Thereto were added 10 ml of ethyl acetate and 5 ml of water. The resulting solution was adjusted to pH 2.0 with 6N hydrochloric acid. The organic layer was separated, washed with a saturated aqueous sodium chloride solution, and then dried over anhydrous magnesium sulfate. Thereafter, the solvent was removed by distillation under reduced pressure. The residue obtained was purified by a column chromatography (eluant: toluene/ethyl acetate=1/1) to obtain 30 mg of N-(4-chlorophenyl)-3-(2,4-difluorophenyl)-2,2-difluoro-3-hydroxy-4-(1H-1,2,4-triazol-1-yl)butanamide.

Melting point: 86.0°–87.0° C.
IR (KBr) cm$^{-1}$: 3400, 1720, 1590, 1490, 1140

EXAMPLES 43–46

The compounds shown in Table 11 were obtained in the same manner as in Example 42. In Table 11, $R^1$, $R^2$, $R^7$ and $R^8$ are those of the following formula:

TABLE 10

| Example No. | $R^1$ | $R^2$ | $R^7$ | $R^8$ | Melting Point (°C.) | IR (KBr) cm$^{-1}$ |
|---|---|---|---|---|---|---|
| 40 |  | F | —CH$_3$ | —CH$_3$ | 85.5–86.5 | 3050, 1655, 1495, 1270 |
| 41 |  | F | H | —OCH$_3$ | 139.5–140.5 | 3455, 1705, 1620, 1140 |

TABLE 11

| Example No. | $R^1$ | $R^2$ | $R^7$ | $R^8$ | Melting Point (°C.) | IR (KBr) cm$^{-1}$ | Remarks |
|---|---|---|---|---|---|---|---|
| 43 |  | F | H | 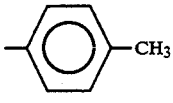 | 187.0–188.0 | 3400, 1700, 1610, 1500 | E |
| 44 |  | F | H | CH$_3$ 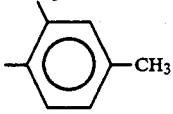 | — | 3405, 1710, 1620, 1505 | |

TABLE 11-continued

Structure:
$$\text{Triazole-N-CH}_2\text{-C(OH)(R}^1\text{)-C(F)(R}^2\text{)-C(=O)-N(R}^7\text{)(R}^8\text{)}$$

| Example No. | $R^1$ | $R^2$ | $R^7$ | $R^8$ | Melting Point (°C.) | IR (KBr) cm$^{-1}$ | Remarks |
| --- | --- | --- | --- | --- | --- | --- | --- |
| 45 | 2,4-difluorophenyl | F | H | 2-methoxyphenyl (OCH$_3$) | 131.5–132.5 | 3400, 1700, 1595, 1530 | |
| 46 | 2,4-difluorophenyl | F | H | pyrazol-methyl (N—NH / N=) | 134.0–138.0 | 3100, 1720, 1580, 1265 | |

EXAMPLE 47

In 2 ml of ethanol was dissolved 160 mg of ethyl 3-(2,4-difluorophenyl)-2,2-difluoro-3-hydroxy-4-(1H-1,2,4-triazol-1-yl)butyrate. To the resulting solution was added 2 ml of a 1N aqueous sodium hydroxide solution at 0°–5° C. The mixture was subjected to reaction at the same temperature for 10 minutes. The reaction mixture was introduced into a mixed solvent consisting of 10 ml of ethyl acetate and 5 ml of water. The resulting solution was adjusted to pH 2.0 with 6N hydrochloric acid. The organic layer was separated, washed with a saturated aqueous sodium chloride solution, and then dried over anhydrous magnesium sulfate. Thereafter, the solvent was removed by distillation under reduced pressure. Diethyl ether was added to the residue obtained, and the resulting crystals were collected by filtration to obtain 100 mg of 3-(2,4-difluorophenyl)-2,2-difluoro-3-hydroxy-4-(1H-1,2,4-triazol-1-yl)butyric acid.

Melting point: 187°–200° C. (decomp.)
IR (KBr) cm$^{-1}$: 3450, 1760, 1610, 1495, 1205

EXAMPLES 48–49

The compounds shown in Table 12 were obtained in the same manner as in Example 47. In Table 12, $R^1$, $R^2$ and $R^3$ are those of the following formula:

EXAMPLE 50

In 20 ml of dioxane were dissolved 300 mg of 3-(2,4-difluorophenyl)-2,2-difluoro-3-hydroxy-4-(1H-1,2,4-triazol-1-yl)butyric acid and 110 mg of N-hydroxysuccinimide. To the resulting solution was added 200 mg of N,N'-dicyclohexylcarbodiimide. Then, the resulting mixture was subjected to reaction at 15°–25° C. for 3 hours. The reaction mixture was subjected to filtration to remove the insolubles, and 4.5 ml of a concentrated aqueous ammonia solution was added to the filtrate. The resulting mixture was subjected to reaction at 15°–25° C. for 20 hours. Then, the solvent was removed by distillation under reduced pressure. To the residue obtained were added 20 ml of ethyl acetate and 10 ml of water. The organic layer was separated, washed with a saturated aqueous sodium chloride solution, and then dried over anhydrous magnesium sulfate. Thereafter, the solvent was removed by distillation under reduced pressure. The residue thus obtained was purified by a column chromatography (eluant: chloroform/methanol=10/1) to obtain 70 mg of 3-(2,4-difluorophenyl)-2,2-difluoro-3-hydroxy-4-(1H-1,2,4-triazol-1-yl)butanamide.

Melting point: 164.5°–165.0° C.
IR (KBr) cm$^{-1}$: 3300, 1690, 1610, 1435, 1270

TABLE 12

$$\text{Triazole-N-CH}_2\text{-C(OH)(R}^1\text{)-C(F)(R}^2\text{)-R}^3$$

| Example No. | $R^1$ | $R^2$ | $R^3$ | Melting Point (°C.) | IR (KBr) cm$^{-1}$ | Remarks |
| --- | --- | --- | --- | --- | --- | --- |
| 48 | 2,4-difluorophenyl | F | —CONH—CH(CH$_3$)COOH | — | 3405, 1700, 1505, 1135 | |
| 49 | 2,4-difluorophenyl | —CH$_2$-phenyl | —COOH | — | 3420, 1615, 1500, 1420 / 3120, 1615, 1500, 1455 | A / B |

EXAMPLES 51-56

The compounds shown in Table 13 were obtained in the same manner as in Example 50. In Table 13, $R^1$, $R^2$, $R^7$ and $R^8$ are those of the following formula:

2,2-difluoro-3-hydroxy-4-(1H-1,2,4-triazol-1-yl)butyrohydrazide.

Melting point: 127.0°-130.0° C.

IR (KBr) cm$^{-1}$: 3330, 1730, 1705, 1590, 1495

TABLE 13

[Structure: triazole-N-CH$_2$-C(OH)(R$^1$)-C(F)(R$^2$)-C(=O)-N(R$^7$)(R$^8$)]

| Example No. | $R^1$ | $R^2$ | $R^7$ | $R^8$ | Melting Point (°C.) | IR (KBr) cm$^{-1}$ | Remarks |
|---|---|---|---|---|---|---|---|
| 51 | 2,4-difluorophenyl | F | —C(CH$_3$)$_3$ | H | 144.5–145.5 | 3440, 1715, 1615, 1530 | |
| 52 | 2,4-difluorophenyl | F | H | 4-cyanophenyl | 108.0–109.5 (decomp.) | 3370, 2230, 1730, 1530 | |
| 53 | 2,4-difluorophenyl | F | H | 2-pyridyl | 117.0–120.0 (decomp.) | 3355, 1700, 1540, 1440 | |
| 54 | 2,4-difluorophenyl | F | H | 3-pyridyl | 119.0–121.0 (decomp.) | 3385, 1705, 1615, 1500 | |
| 55 | 2,4-difluorophenyl | F | H | —CH(CH$_3$)CONH-cyclopropyl | 112.0–115.0 (decomp.) | 3315, 1700, 1665, 1505 | |
| 56 | 2,4-difluorophenyl | —CH$_2$-phenyl | H | H | 121.5–124.0 | 3495, 1685, 1500, 1270 | A |
| | | | | | 204.5–205.5 | 3470, 1680, 1500, 1275 | B |

EXAMPLE 57

In 7 ml of dichloromethane was suspended 0.33 g of 3-(2,4-difluorophenyl)-2,2-difluoro-3-hydroxy-4-(1H-1,2,4-triazol-1-yl)butyrohydrazide. To the suspension was added 0.12 g of triethylamine. Thereto was dropwise added 0.19 g of 4-fluorobenzoyl chloride at 5°-10° C. The resulting mixture was subjected to reaction at the same temperature for 1 hour. The reaction mixture was introduced into a mixed solvent consisting of 10 ml of dichloromethane and 10 ml of water. The resulting solution was adjusted to pH 1.0 with 6N hydrochloric acid. The organic layer was separated, washed with a saturated aqueous sodium chloride solution, and then dried over anhydrous magnesium sulfate. Thereafter, the solvent was removed by distillation under reduced pressure. The residue thus obtained was purified by a column chromatography (eluant: chloroform) to obtain 0.25 g of N'-(4-fluorobenzoyl)-3-(2,4-difluorophenyl)-

EXAMPLE 58

In 4 ml of methylene chloride was dissolved 80 mg of N-(2-methoxyphenyl)-3-(2,4-difluorophenyl)-2,2-difluoro-3-hydroxy-4-(1H-1,2,4-triazol-1-yl)butanamide. To the resulting solution were added 120 mg of ethanethiol and 130 mg of aluminum chloride at −5° to 0° C. The resulting mixture was subjected to reaction at 20°-25° C. for 20 hours. Then, the reaction mixture was introduced into a mixed solvent consisting of 10 ml of chloroform and 5 ml of water. The resulting solution was adjusted to pH 2.0 with 6N hydrochloric acid. The organic layer was separated, washed with a saturated aqueous sodium chloride solution, and then dried over anhydrous magnesium sulfate. Thereafter, the solvent was removed by distillation under reduced pressure. The residue thus obtained was purified by a column chromatography (eluant: chloroform/methanol=20/1) to obtain 30 mg of N-(2-hydroxyphenyl)-3-(2,4- difluorophenyl)-2,2-difluoro-3-hydroxy-4-(1H-1,2,4-triazol-1-yl)butanamide.
Melting point: 121.0°–126.0° C.
IR (KBr) cm$^{-1}$: 3420, 1690, 1540, 1455, 1270

EXAMPLE 59

In 5 ml of pyridine was dissolved 150 mg of 3-(2,4-difluorophenyl)-2,2-difluoro-3-hydroxy-4-(1H-1,2,4-triazol-1-yl)butanamide. To the solution was added 100 mg of trichloroacetyl chloride at 0°–5° C. The resulting mixture was subjected to reaction at the same temperature for 2 hours. Then, the reaction mixture was introduced into a mixed solvent consisting of 10 ml of ethyl acetate and 5 ml of water. The resulting solution was adjusted to pH 2.0 with 6N hydrochloric acid. The organic layer was separated, washed with a saturated aqueous sodium chloride solution, and then dried over anhydrous magnesium sulfate. Thereafter, the solvent was removed by distillation under reduced pressure. The residue thus obtained was purified by a column chromatography (eluant: chloroform/methanol=50/1) to obtain 100 mg of 3-(2,4-difluorophenyl)-2,2-difluoro-3-hydroxy-4-(1H-1,2,4-triazol-1-yl)butanenitrile.
Melting point: 130.5°–131.5° C.
IR (KBr) cm$^{-1}$: 3120, 2250, 1605, 1420, 1115

EXAMPLES 60–61

The compounds shown in Table 14 were obtained in the same manner as in Example 59. In Table 14, $R^1$, $R^2$ and $R^3$ are those of the following formula:

TABLE 14

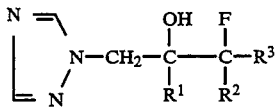

| Example No. | $R^1$ | $R^2$ | $R^3$ | Melting Point (°C.) | IR (KBr) cm$^{-1}$ | Remarks |
|---|---|---|---|---|---|---|
| 60 | F-phenyl-F | H | —CN | 144.5–145.0 | 3100, 1615, 1495, 1270 | A |
| 61 | F-phenyl-F | —CH$_3$ | —CN | — | 3445, 1610, 1505, 1090 | A |

EXAMPLE 62

To 100 mg of 3-(2,4-difluorophenyl)-2,2-difluoro-3-hydroxy-4-(1H-1,2,4-triazol-1-yl)butanenitrile were added 0.2 ml of diethyl dithiophosphate and 0.04 ml of water. The resulting mixture was subjected to reaction at 80°–90° C. for 5 hours. The reaction mixture was purified by a column chromatography (eluant: chloroform/methanol=50/1) to obtain an oily matter. To the oily matter was added 0.5 ml of a 2N hydrochloric acid-dioxane solution, and then diethyl ether was added. The resulting crystals were collected by filtration to obtain 110 mg of 3-(2,4-difluorophenyl)-2,2-difluoro-3-hydroxy-4-(1H-1,2,4-triazol-1-yl)butanethioamide hydrochloride.
Melting point: 178° C. (decomp.)
IR (KBr) cm$^{-1}$: 3420, 1625, 1505, 1425, 1140

EXAMPLE 63

In 6 ml of chloroform was dissolved 300 mg of 3-(2,4-difluorophenyl)-2,2-difluoro-3-hydroxy-4-(1H-1,2,4-triazol-1-yl)butanenitrile. To the resulting solution were added 83 mg of hydroxylamine hydrochloride and 100 mg of triethylamine at 0°–5° C. The resulting mixture was subjected to reaction at 20°–25° C. for 3 hours. The reaction mixture was introduced into a mixed solvent consisting of 10 ml of chloroform and 5 ml of water. The resulting solution was adjusted to pH 9.0 with a saturated aqueous sodium hydrogencarbonate solution. The organic layer was separated, washed with a saturated aqueous sodium chloride solution, and then dried over anhydrous magnesium sulfate. Thereafter, the solvent was removed by distillation under reduced pressure to obtain 330 mg of 3-(2,4-difluorophenyl)-2,2-difluoro-3-hydroxy-4-(1H-1,2,4-triazol-1-yl)butanamide oxime.
IR (KBr) cm$^{-1}$: 3340, 1665, 1490, 1265, 1135

EXAMPLE 64

3-(2,4-Difluorophenyl)-2,2-difluoro-3-hydroxy-4-(1H-1,2,4-triazol-1-yl)butanamide O-methyloxime was obtained in the same manner as in Example 63.
Melting point: 113.5°–114.5° C.
IR (KBr) cm$^{-1}$: 3365, 1645, 1505, 1275, 1105

EXAMPLE 65

In 2 ml of methanol was dissolved 100 mg of 3-(2,4-difluorophenyl)-2,2-difluoro-3-hydroxy-4-(1H-1,2,4-triazol-1-yl)butanenitrile. The solution was refluxed for 6 hours. Then, the solvent was removed by distillation under reduced pressure, and diisopropyl ether was added to the residue obtained. The resulting crystals were collected by filtration to obtain 90 mg of methyl 3-(2,4-difluorophenyl)-2,2-difluoro-3-hydroxy-4-(1H-1,2,4-triazol-1-yl)butylimidate.
Melting point: 115.5°–116.5° C.
IR (KBr) cm$^{-1}$: 3300, 1670, 1610, 1495, 1115

EXAMPLE 66

In 1 ml of chloroform was dissolved 90 mg of methyl 3-(2,4-difluorophenyl)-2,2-difluoro-3-hydroxy-4-(1H-1,2,4-triazol-1-yl)butylimidate. To the solution was added 90 mg of cyclopropylamine. The resulting mixture was refluxed for 3 hours. The solvent was removed by distillation under reduced pressure. The residue thus obtained was purified by a column chromatography (eluant: chloroform/methanol=20/1) to obtain an oily matter. To the oily matter was added 0.5 ml of a 2N hydrochloric acid-dioxane solution, and acetone was then added. The resulting crystals were collected by filtration to obtain 20 mg of N-cyclopropyl-3-(2,4-difluorophenyl)-2,2-difluoro-3-hydroxy-4-(1H-1,2,4-triazol-1-yl)-butanamidine dihydrochloride.

Melting point: 229.5°-230.5° C.
IR (KBr) cm$^{-1}$: 3300, 1665, 1605, 1495, 1270

EXAMPLE 67

In 4 ml of a 6N ammonia-methanol solution was dissolved 100 mg of 3-(2,4-difluorophenyl)-2,2-difluoro-3-hydroxy-4-(1H-1,2,4-triazol-1-yl)butanenitrile. The solution was subjected to reaction at 70° C. for 7 hours in a sealed tube. The solvent was removed by distillation under reduced pressure. The residue thus obtained was purified by a column chromatography (eluant: chloroform/methanol=10/1). To the purified residue was added 0.5 ml of a 2N hydrochloric acid-dioxane solution, and dioxane was thereafter added. The resulting crystals were collected by filtration to obtain 50 mg of a dioxane adduct of 3-(2,4-difluorophenyl)-2,2-difluoro-3-hydroxy-4-(1H-1,2,4-dihydrochloride.

Melting point: 109.5°-110.5° C.
IR (KBr) cm$^{-1}$: 3420, 1715, 1620, 1505, 1150

EXAMPLE 68

In 5 ml of ethanol was dissolved 1.0 g of ethyl 4-chloro-2,2-difluoro-3-hydroxy-3-phenylbutyrate. To the resulting solution was added 0.98 ml of a concentrated aqueous ammonia. The solution was subjected to reaction at 25°30° C. for 3 hours. The solvent was removed by distillation under reduced pressure. To the residue obtained were added 20 ml of ethyl acetate and 20 ml of water. The resulting solution was adjusted to pH 1.0 with 6N hydrochloric acid. The organic layer was separated, washed with a saturated aqueous sodium chloride solution, and then dried over anhydrous magnesium sulfate. Thereafter, the solvent was removed by distillation under reduced pressure. The residue obtained was dissolved in 10 ml of N,N-dimethylformamide. To the solution were added 0.5 g of 1,2,4-triazole and 1.0 g of anhydrous potassium carbonate. The resulting mixture was subjected to reaction at 70° C. for 10 hours. Then, the solvent was removed by distillation under reduced pressure. To the residue obtained were added 20 ml of ethyl acetate and 20 ml of water. The resulting solution was adjusted to pH 1.0 with 6N hydrochloric acid. The organic layer was separated, washed with a saturated aqueous sodium chloride solution, and then dried over anhydrous magnesium sulfate. Thereafter, the solvent was removed by distillation under reduced pressure. The residue thus obtained was purified by a column chromatography (eluant:-chloroform/methanol=50/1) to obtain 0.30 g of 2,2-difluoro-3-hydroxy-3-phenyl-4-(1H-1,2,4-triazol-1-yl)butanamide.

Melting point: 160.5°-161.0° C.
IR (KBr) cm$^{-1}$: 3325, 1700, 1510, 1185

EXAMPLES 69-102

The compounds shown in Table 15 were obtained in the same manner as in Example 68. In Table 15, $R^1$, $R^7$ and $R^8$ are those of the following formula:

TABLE 15

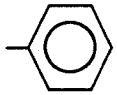

| Example No. | $R^1$ | $R^7$ | $R^8$ | Melting Point (°C.) | IR (KBr) cm$^{-1}$ |
|---|---|---|---|---|---|
| 69 | 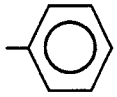 | —CH$_2$CH$_3$ | H | 160.0–161.5 | 3275, 1690, 1510, 1105 |
| 70 | 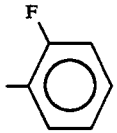 | 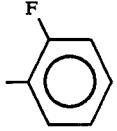 | H | 96.5–97.0 | 3290, 1695, 1510, 1110 |
| 71 | F-◯ | H | H | 168.0–169.0 | 3165, 1675, 1215, 1115 |
| 72 | F-◯ | —CH$_3$ | H | 151.5–152.5 | 3315, 1685, 1220, 1110 |

TABLE 15-continued

[Structure: N=CH-N(CH=N)-CH₂-C(OH)(R¹)-C(F)(F)-C(=O)-N(R⁷)(R⁸)]

| Example No. | R¹ | R⁷ | R⁸ | Melting Point (°C.) | IR (KBr) cm⁻¹ |
|---|---|---|---|---|---|
| 73 | 2-F-C₆H₄ | —CH₂CH₃ | H | 122.5–123.5 | 3275, 1675, 1515, 1140 |
| 74 | 2-Cl-C₆H₄ | —CH₃ | H | 147.5–148.0 | 3325, 1685, 1510, 1135 |
| 75 | 2-Cl-C₆H₄ | —CH₂CH₃ | H | 107.0–108.0 | 3275, 1675, 1510, 1135 |
| 76 | 2,6-F₂-C₆H₃ | H | H | 164.5–165.0 | 3395, 1730, 1620, 1140 |
| 77 | 2,6-F₂-C₆H₃ | —CH₂CH₃ | H | 114.0–114.5 | 3480, 1680, 1625, 1140 |
| 78 | 2,6-F₂-C₆H₃ | cyclopropyl | H | 145.5–146.0 | 3475, 1675, 1625, 1135 |
| 79 | 2-Cl-4-F-C₆H₃ | H | H | 133.0–134.0 | 3320, 1710, 1600, 1580 |
| 80 | 2-Cl-4-F-C₆H₃ | —CH₃ | H | 143.5–144.5 | 3340, 1685, 1600, 1145 |
| 81 | 2-Cl-4-F-C₆H₃ | —CH₂CH₃ | H | 105.0–106.0 | 3345, 1680, 1510, 1145 |

TABLE 15-continued
$$\underset{N=\!\!\!=\!N}{\overset{N=\!\!\!=\!\!\!=}{\underset{|}{N}}}\!\!-\!CH_2\!-\!\underset{R^1}{\overset{OH}{\underset{|}{C}}}\!-\!\underset{F}{\overset{F}{\underset{|}{C}}}\!-\!\overset{O}{\underset{|}{C}}\!-\!N\!\!<\!\!\overset{R^7}{\underset{R^8}{}}$$
| Example No. | R¹ | R⁷ | R⁸ | Melting Point (°C.) | IR (KBr) cm⁻¹ |
|---|---|---|---|---|---|
| 82 | 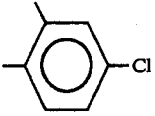 | H | H | 181.5–183.0 | 3315, 1705, 1615, 1180 |
| 83 | 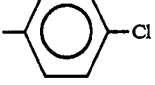 | —CH₂CH₃ | H | 128.5–129.5 | 3260, 1675, 1515, 1120 |
| 84 | 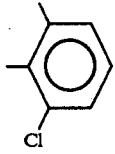 | H | H | 195.0–196.0 | 3515, 1720, 1435, 1135 |
| 85 | 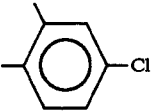 | 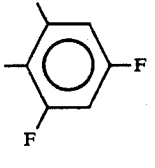 | H | 137.5–138.5 | 3245, 1685, 1510, 1025 |
| 86 | 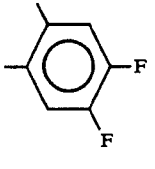 | H | H | 148.0–149.0 | 3485, 1715, 1600, 1125 |
| 87 | 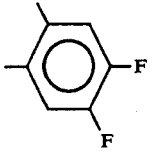 | H | H | 155.5–156.5 | 3325, 1700, 1515, 1105 |
| 88 | 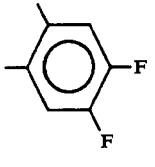 | —CH₂CH₃ | H | 147.0–148.0 | 3445, 1710, 1515, 1120 |
| 89 | 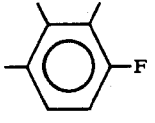 | ◁ | H | 165.0–166.0 | 3450, 1710, 1515, 1120 |
| 90 | F F<br>—⌬<br>F | H | H | 227.5–228.0 | 3440, 1715, 1515, 1475 |

TABLE 15-continued

[Structure: N=N-N(CH₂-)-CH₂-C(OH)(R¹)-CF₂-C(O)-N(R⁷)(R⁸)]

| Example No. | R¹ | R⁷ | R⁸ | Melting Point (°C.) | IR (KBr) cm⁻¹ |
|---|---|---|---|---|---|
| 91 | 2,3,4-trifluorophenyl | —CH₂CH₃ | H | 97.5–99.0 | 3275, 1690, 1515, 1140 |
| 92 | 2,3,4-trifluorophenyl | cyclopropyl | H | 118.5–119.5 | 3220, 1675, 1510, 1115 |
| 93 | 2-Cl-4,5-difluorophenyl | H | H | 137.5–139.0 | 3245, 1705, 1500, 1110 |
| 94 | 2-Cl-4,5-difluorophenyl | —CH₂CH₃ | H | 142.5–143.0 | 3445, 1710, 1495, 1125 |
| 95 | 2-Cl-4,5-difluorophenyl | cyclopropyl | H | 150.5–151.5 | 3455, 1710, 1495, 1125 |
| 96 | 2-F-4-CF₃-phenyl | H | H | 147.5–148.5 | 3485, 1700, 1425, 1335 |
| 97 | 2-F-4-CF₃-phenyl | —CH₂CH₃ | H | 128.0–129.0 | 3280, 1680, 1425, 1335 |
| 98 | 2-F-4-CF₃-phenyl | cyclopropyl | H | 159.5–160.5 | 3315, 1675, 1335, 1135 |
| 99 | 2-Cl-4-F-5-CH₃-phenyl | H | H | 123.0–124.0 | 3300, 1700, 1510, 1285 |

TABLE 15-continued $$\text{N}=\text{N}-\text{CH}_2-\underset{\underset{R^1}{|}}{\overset{\overset{OH}{|}}{C}}-\underset{\underset{F}{|}}{\overset{\overset{F}{|}}{C}}-\overset{\overset{O}{\|}}{C}-\text{N}\underset{R^8}{\overset{R^7}{}}$$

| Example No. | R$^1$ | R$^7$ | R$^8$ | Melting Point (°C.) | IR (KBr) cm$^{-1}$ |
|---|---|---|---|---|---|
| 100 | 4-Cl-3-F-5-CH$_3$-phenyl | —CH$_2$CH$_3$ | H | 105.0–105.5 | 3290, 1675, 1510, 1140 |
| 101 | 4-OCF$_3$-phenyl | H | H | 128.0–128.5 | 3335, 1700, 1515, 1255 |
| 102 | 2-OCH$_3$-phenyl | H | H | 134.5–135.0 | 3165, 1715, 1490, 1125 |

EXAMPLES 103–129

The compounds shown in Table 16 were obtained in the same manner as in Example 10. In Table 16, R$^1$, R$^7$ and R$^8$ are those of the following formula:

TABLE 16

$$\text{N}=\text{N}-\text{CH}_2-\underset{\underset{R^1}{|}}{\overset{\overset{OH}{|}}{C}}-\underset{\underset{F}{|}}{\overset{\overset{F}{|}}{C}}-\overset{\overset{O}{\|}}{C}-\text{N}\underset{R^8}{\overset{R^7}{}}$$

| Example No. | R$^1$ | R$^7$ | R$^8$ | Melting Point (°C.) | IR (KBr) cm$^{-1}$ | Remarks |
|---|---|---|---|---|---|---|
| 103 | 4-F-phenyl | H | H | 182.0–183.0 | 3320, 1700, 1515, 1085 | |
| 104 | 4-F-phenyl | —CH$_2$CH$_3$ | H | 173.0–173.5 | 3265, 1685, 1515, 1095 | |
| 105 | 4-F-phenyl | cyclopropyl | H | 125.0–126.0 | 3430, 1700, 1520, 1135 | |
| 106 | 4-Cl-phenyl | H | H | 180.5–181.5 | 3300, 1700, 1180, 1090 | |
| 107 | 4-Cl-phenyl | —CH$_2$CH$_3$ | H | 122.0–122.5 | 3280, 1695, 1510, 1095 | |

TABLE 16-continued $$\text{N=}\!\!\!\overset{\displaystyle\diagup\!\!\!=\!\!\!\text{N}}{\underset{\displaystyle\diagdown\!\!\!=\!\!\!\text{N}}{\text{N}}}\!\!-\!\text{CH}_2\!-\!\underset{\underset{\displaystyle R^1}{|}}{\overset{\overset{\displaystyle \text{OH}}{|}}{\text{C}}}\!-\!\underset{\underset{\displaystyle F}{|}}{\overset{\overset{\displaystyle F}{|}}{\text{C}}}\!-\!\overset{\overset{\displaystyle O}{\|}}{\text{C}}\!-\!\text{N}\!\!\begin{array}{c}R^7\\ \\R^8\end{array}$$

| Example No. | R¹ | R⁷ | R⁸ | Melting Point (°C.) | IR (KBr) cm⁻¹ | Remarks |
|---|---|---|---|---|---|---|
| 108 | 4-Cl-phenyl | cyclopropyl | H | 129.0–130.0 | 3380, 1690, 1510, 1120 | |
| 109 | 3-Cl-phenyl | H | H | 154.5–155.5 | 3460, 1700, 1505, 1430 | |
| 110 | 3-Cl-phenyl | —CH₂CH₃ | H | 106.5–108.0 | 3275, 1695, 1510, 1110 | |
| 111 | 2,4-F₂-phenyl | —CH₂CH₂F | H | 114.0–114.5 | 3450, 1710, 1620, 1130 | |
| 112 | 2,4-F₂-phenyl | —CH₂CH₂CH₂F | H | 111.0–112.0 | 3335, 1680, 1505, 1110 | |
| 113 | 2,4-F₂-phenyl | —CH(CH₃)CH₂CH₃ | H | 96.0–96.5 | 3445, 1705, 1530, 1115 | |
| 114 | 2,4-F₂-phenyl | —CH₂CH₂CH₂CH₃ | H | — | 3330, 1695, 1540, 1505 | |
| 115 | 2,4-F₂-phenyl | —CH(CH₃)CH₂OH | H | — | 3435, 1685, 1505, 1140 | |
| 116 | 2,4-F₂-phenyl | H | H | 169.5–171.5 | 3310, 1700, 1495, 1435 | |
| 117 | 2,4-F₂-phenyl | —CH₂CH₃ | H | 113.5–114.5 | 3300, 1685, 1490, 1170 | |

TABLE 16-continued
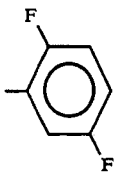
| Example No. | R¹ | R⁷ | R⁸ | Melting Point (°C.) | IR (KBr) cm⁻¹ | Remarks |
|---|---|---|---|---|---|---|
| 118 |  | 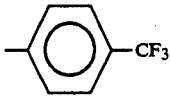 | H | 134.5–135.5 | 3335, 1675, 1495, 1110 | |
| 119 | 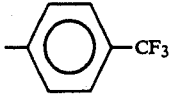 | H | H | 147.0–148.0 | 3425, 1700, 1330, 1130 | |
| 120 | 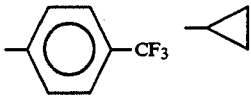 | —CH₂CH₃ | H | 139.0–140.0 | 3280, 1700, 1510, 1330 | |
| 121 |  | 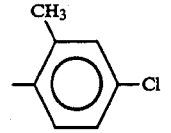 | H | 142.5–143.5 | 3390, 1690, 1510, 1335 | |
| 122 | 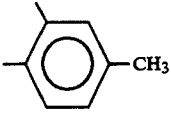 | H | H | 185.0–186.0 | 3320, 1700, 1510, 1095 | |
| 123 | 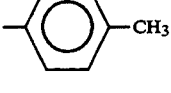 | H | H | 148.5–150.5 | 3320, 1705, 1510, 1175 | |
| 124 | 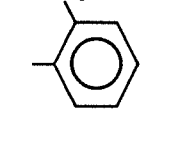 | H | H | 176.0–176.5 | 3475, 1705, 1515, 1090 | |
| 125 |  | H | H | 182.5–183.5 | 3360, 1700, 1510, 1090 | |
| 126 | 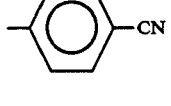 | H | H | 123.5–124.0 | 3270, 1715, 1515, 1095 | |
| 127 | 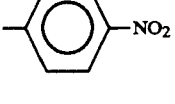 | H | H | 182.5–183.0 | 3450, 2235, 1720, 1095 | |
| 128 | —⟨⟩—NO₂ | H | H | 238.5–242.0 | 3445, 1715, 1520, 1355 | |

TABLE 16-continued $$\underset{N}{\overset{N=\\}{\underset{\phantom{N}}{\bigsqcup}}}N-CH_2-\underset{R^1}{\overset{OH}{\underset{|}{C}}}-\underset{F}{\overset{F}{\underset{|}{C}}}-\overset{O}{\underset{\phantom{|}}{\overset{\|}{C}}}-N\underset{R^8}{\overset{R^7}{\diagdown}}$$

| Example No. | R¹ | R⁷ | R⁸ | Melting Point (°C.) | IR (KBr) cm⁻¹ | Remarks |
|---|---|---|---|---|---|---|
| 129 | 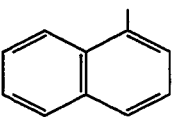 | H | H | — | 3395, 1710, 1600, 1560 | G |

EXAMPLES 130–132

The compounds shown in Table 17 were obtained in the same manner as in Example 39.

In Examples 131 and 132, the separation of diastereomers into individual components can be conducted by a column chromatography (eluant: toluene/ethyl acetate=3/1).

In Table 17, R¹ and R⁴ are those of the following formula:

sodium carbonate. The aqueous layer was separated and 20 ml of ethyl acetate was added thereto. The resulting mixture was adjusted to pH 1.0 with 6N hydrochloric acid. The organic layer was separated, washed with a saturated aqueous sodium chloride solution, and then dried over anhydrous magnesium sulfate. Thereafter, the solvent was removed by distillation under reduced pressure to obtain 230 mg of 3-(2,4-difluorophenyl)-2,2-difluoro-3-hydroxy-4-(1H-1,2,4-triazol-1-yl)butyric acid.

TABLE 17

$$\underset{N}{\overset{N=\\}{\underset{\phantom{N}}{\bigsqcup}}}N-CH_2-\underset{R^1}{\overset{OH}{\underset{|}{C}}}-\underset{F}{\overset{F}{\underset{|}{C}}}-\overset{O}{\underset{\phantom{|}}{\overset{\|}{C}}}-R^4$$

| Example No. | R¹ | R⁴ | Melting Point (°C.) | IR (KBr) cm⁻¹ | Remarks |
|---|---|---|---|---|---|
| 130 | 2-Cl-4-F-phenyl | —N(morpholino)O | 137.0–138.0 | 3405, 1655, 1135, 1115 | |
| 131 | 2-Cl-4-F-phenyl | —N-(tetrahydrofuranyl-2-carbonyl)-NH-phenyl | Amorphous<br>Amorphous | 3315, 1650, 1445, 1135<br>3315, 1655, 1445, 1135 | A<br>B |
| 132 | 2,4-F₂-phenyl | —N-(tetrahydrofuranyl-2-carbonyl)-NH-phenyl | Amorphous<br>Amorphous | 3310, 1650, 1505, 1140<br>3315, 1650, 1500, 1140 | A<br>B |

EXAMPLE 133

To 4 ml of 47% hydrobromic acid was added 500 mg of N-(4-chlorobenzyl)-3-(2,4-difluorophenyl)-2,2-difluoro-3-hydroxy-4-(1H-1,2,4-triazol-1-yl)butanamide. The resulting mixture was refluxed for 6 hours. Thereto were added 20 ml of toluene and 20 ml of water. The resulting solution was adjusted to pH 8.5 with Melting point: 187°–200° C. (decomp.)
IR (KBr) cm⁻¹: 3450, 1760, 1610, 1495, 1205

EXAMPLES 134–135

The compounds shown in Table 18 were obtained in the same manner as in Example 133, using the diastereomers A obtained in Example 131 and Example 132.

In Table 18, R¹ is that of the following formula:

TABLE 18

Structure:

$$\text{pyrazolyl-N-CH}_2\text{-C(OH)(R}^1\text{)-C(F)}_2\text{-C(=O)-OH}$$

| Example No. | R¹ | Melting Point (°C.) | IR (KBr) cm⁻¹ | $[\alpha]_D^{25}$ | Remarks |
|---|---|---|---|---|---|
| 134 | 2,4-difluorophenyl | Amorphous | 3145, 1735, 1505, 1145 | — | F |
| 135 | 3-chloro-4-fluorophenyl | 102.5–104.5 | 3235, 1760, 1600, 1485 | −30.7° (C = 1.00, EtOH) | FH |

EXAMPLES 136–148

The compounds shown in Table 19 were obtained in the same manner as in Example 50.

The optically active compounds of Examples 142–148 were produced from the compounds obtained in Examples 134–135.

In Table 19, R¹, R⁷ and R⁸ are those of the following formula:

TABLE 19

Structure:

$$\text{pyrazolyl-N-CH}_2\text{-C(OH)(R}^1\text{)-C(F)}_2\text{-C(=O)-N(R}^7\text{)(R}^8\text{)}$$

| Example No. | R¹ | R⁷ | R⁸ | Melting Point (°C.) | IR (KBr) cm⁻¹ | $[\alpha]_D^{25}$ | Remarks |
|---|---|---|---|---|---|---|---|
| 136 | 2,4-difluorophenyl | 4-CF₃-phenyl | H | 158.0–159.0 | 3365, 1690, 1325, 1065 | — | |
| 137 | 2,4-difluorophenyl | 4-CN-phenyl | H | 176.5–177.0 | 3360, 2230, 1720, 1555 | — | |
| 138 | 2,4-difluorophenyl | 4-CH₂CN-phenyl | H | 154.0–154.5 | 3290, 2265, 1700, 1100 | — | |
| 139 | 2,4-difluorophenyl | 4-OMe-phenyl | H | 125.5–126.0 | 3445, 1680, 1510, 1130 | — | |
| 140 | 2,4-difluorophenyl | 3-methyl-isoxazol-5-yl | H | 182.5–184.0 | 3440, 1710, 1620, 1150 | — | |

TABLE 19-continued $$\underset{N}{\overset{N=}{\underset{\parallel}{\bigvee}}}N-CH_2-\underset{R^1}{\overset{OH}{\underset{|}{C}}}-\underset{F}{\overset{F}{\underset{|}{C}}}-\underset{}{\overset{O}{\underset{\parallel}{C}}}-N\underset{R^8}{\overset{R^7}{}}$$

| Example No. | R¹ | R⁷ | R⁸ | Melting Point (°C.) | IR (KBr) cm⁻¹ | $[\alpha]_D^{25}$ | Remarks |
|---|---|---|---|---|---|---|---|
| 141 | 2,4-difluorophenyl | −C(CH₃)₂−CH₂OH | H | 135.5–136.0 | 3330, 1690, 1510, 1110 | — | |
| 142 | 2,4-difluorophenyl | H | H | 57.0–62.0 | 3335, 1700, 1615, 1420 | −42.5° (C = 1.00, EtOH) | F |
| 143 | 2,4-difluorophenyl | −CH₃ | H | Amorphous | (neat) 3330, 1695, 1505, 1145 | −39.4° (C = 2.04, EtOH) | F |
| 144 | 2,4-difluorophenyl | −CH₂CH₃ | H | Oily | (neat) 3360, 1695, 1615, 1505 | −34.8° (C = 1.00, EtOH) | F |
| 145 | 2,4-difluorophenyl | cyclopropyl | H | 148.0–151.0 | 3305, 1695, 1620, 1600 | −10.7° (C = 1.00, CHCl₃) | F |
| 146 | 2-chloro-4-fluorophenyl | H | H | 207.0–214.0 | 3485, 1715, 1605, 1490 | −42.5° (C = 1.00, EtOH) | FG |
| 147 | 2-chloro-4-fluorophenyl | −CH₃ | H | 110.0–111.0 | 3440, 1705, 1560, 1100 | −25.0° (C = 0.92, EtOH) | F |
| 148 | 2-chloro-4-fluorophenyl | cyclopropyl | H | 187.5–188.0 | 3310, 1695, 1550, 1140 | −15.0° (C = 1.20, EtOH) | F |

EXAMPLE 149

N-(4-hydroxyphenyl)-3-(2,4-difluorophenyl)-2,2-difluoro-3-hydroxy-4-(1H-1,2,4-triazol-1-yl)butanamide was obtained in the same manner as in Example 58 from the compound obtained in Example 139.

Melting point: 115.0–°117.0° C.
IR (KBr) cm⁻¹: 3385, 1695, 1515, 1140

EXAMPLE 150

In 2 ml of N,N-dimethylformamide was dissolved 0.1 g of N-(1-hydroxy-2-methylpropan-2-yl)-3-(2,4-difluorophenyl)-2,2-difluoro-3-hydroxy-4-(1H-1,2,4-triazol-1-yl)butanamide. To the resulting solution was added 0.012 g of 60% sodium hydride at 0°–5° C. The solution was subjected to reaction at 20°–25° C. for 30 minutes. To the reaction mixture was added 0.04 g of methyl iodide at 0°–5° C. The resulting mixture was subjected to reaction at 20°–25° C. for 12 hours. The reaction mixture was introduced into a mixed solvent consisting of 10 ml of ethyl acetate and 5 ml of water. The resulting solution was adjusted to pH 2.0 with 6N hydrochloric acid. The organic layer was separated, washed with a saturated aqueous sodium chloride solution, and then dried over anhydrous magnesium sulfate. Thereafter, the solvent was removed by distillation under reduced pressure. The residue thus obtained was purified by a column chromatography (eluant: chloroform/methanol=100/1) to obtain 30 mg of N-(1-methoxy-2-methylpropan-2-yl)-3-(2,4-difluorophenyl)-2,2-difluoro-3-hydroxy-4-(1H-1,2,4-triazol-1-yl)butanamide.

IR (neat) cm$^{-1}$: 3395, 1700, 1510, 1090

EXAMPLE 151

To 10 ml of dried tetrahydrofuran were added 0.36 g of N-(2-hydroxyethyl)-3-(2,4-difluorophenyl)-2,2-difluoro-3-hydroxy-4-(1H-1,2,4-triazol-1-yl)butanamide, 0.39 g of triphenylphosphine and 0.26 g of diethyl azodicarboxylate. The resulting mixture was subjected to reaction at 20°-25° C. for 12 hours. The reaction mixture was introduced into a mixed solvent consisting of 20 ml of ethyl acetate and 10 ml of water. The resulting solution was adjusted to pH 2.0 with 6N hydrochloric acid. The organic layer was separated, washed with a saturated aqueous sodium chloride solution, and then dried over anhydrous magnesium sulfate. Thereafter, the solvent was removed by distillation under reduced pressure. The residue thus obtained was purified by a column chromatography (eluant: toluene/ethyl acetate=10/1) to obtain 0.13 g of 1-aziridinylcarbonyl-2-(2,4-difluorophenyl)-1,1-difluoro-2-hydroxy-3-(1H-1,2,4-triazol-1-yl)propane.

Melting point: 87.5°-88.0° C.
IR (KBr) cm$^{-1}$: 3415, 1680, 1615, 1080

What is claimed is:

1. A triazole derivative represented by the formula (1) or its salt:

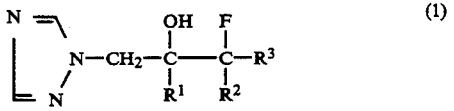

wherein R$^1$ represents a substituted or unsubstituted phenyl or naphthyl group; R$^2$ represents a fluorine atom; and R$^3$ represents a group of the formula

in which R$^4$ is a group of the formula

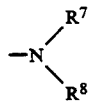

(R$^7$ and R$^8$, which may be the same or different, are hydrogen atoms or substituted or unsubstituted C$_{1-10}$ alkyl, C$_{2-10}$ alkenyl, C$_{2-10}$ alkynyl, C$_{3-8}$ cycloalkyl, phenyl, naphthyl, amino, C$_{1-10}$ alkoxy or hydroxyl groups), wherein the phenyl and naphthyl groups for R$^1$; the C$_{1-10}$ alkyl group for R$^2$; and the C$_{1-10}$ alkyl, C$_{1-10}$ alkenyl, C$_{2-10}$ alkynyl, C$_{3-8}$ cycloalkyl, phenyl, naphthyl, amino, C$_{1-10}$ alkoxy and hydroxy groups for R$^7$ and R$^8$ may each be substituted by at least one substituent selected from the group consisting of halogen atoms, unsubstituted or cyano-substituted C$_{1-4}$ alkyl groups, C$_{1-4}$ alkoxy groups, halo-C$_{1-4}$ alkoxy groups, C$_{1-4}$ alkylthio groups, C$_{1-4}$ alkoxycarbonyl groups, hydroxyl group, mercapto group, carboxyl group, amino group, N—C$_{1-4}$ alkylamino groups, N,N-di-C$_{1-4}$ alkylamino groups, cyano group, nitro group, halo-C$_{1-4}$ alkyl groups, unsubstituted or halogen-substituted phenyl groups, unsubstituted or halogen-substituted naphthyl groups, unsubstituted or halogen-substituted formyl groups, unsubstituted or halogen-substituted C$_{2-10}$ alkanoyl groups unsubstituted or halogen-substituted benzoyl groups and unsubstituted or C$_{1-10}$ alkyl-, C$_{3-8}$ cycloalkyl-, phenyl- or naphthyl-substituted carbamoyl groups.

2. The triazole derivative or its salt according to claim 1, wherein each of the substituted phenyl or naphthyl group in the definition of R$^1$; and the substituted C$_{1-10}$ alkyl, C$_{2-10}$ alkenyl, C$_{2-10}$ alkynyl, C$_{3-8}$ cycloalkyl, phenyl, naphthyl, amino, C$_{1-10}$ alkoxy or hydroxyl group in the definitions of R$^7$ and R$^8$ has at least one substituent selected from the group consisting of halogen atoms, unsubstituted or cyano-substituted C$_{1-4}$ alkyl groups, C$_{1-4}$ alkoxy groups, halo-C$_{1-4}$ alkoxy groups, C$_{1-4}$ alkylthio groups, N,N-di-C$_{1-4}$ alkoxycarbonyl groups, hydroxyl group, mercapto group, carboxyl groups, amino group, N—C$_{1-4}$ alkylamino groups, N,N-di-C$_{1-4}$ alkylamino groups, cyano group, nitro group, halo-C$_{1-4}$ alkyl groups, unsubstituted or halogen-substituted phenyl groups, unsubstituted or halogen-substituted naphthyl groups, unsubstituted or halogen-substituted formyl groups, unsubstituted or halogen-substituted C$_{2-10}$ alkanoyl groups and unsubstituted or C$_{1-10}$ alkyl-, C$_{3-8}$ cycloalkyl-, phenyl- or naphthyl-substituted carbamoyl groups.

3. The triazole derivative or its salt according to claim 1, wherein each of the substituted phenyl or naphthyl group in the definition of R$^1$; alkyl group in the definitions of R$^2$ and R$^6$; and the substituted C$_{1-10}$ alkyl, C$_{2-10}$ alkenyl, C$_{2-10}$ alkynyl, C$_{3-8}$ cycloalkyl, phenyl, naphthyl, amino, C$_{1-10}$ alkoxy or hydroxyl group in the definitions of R$^7$ and R$^8$ has at least one substituent selected from the group consisting of halogen atoms, C$_{1-4}$ alkyl groups, C$_{1-4}$ alkoxy groups, C$_{1-4}$ alkylthio groups, C$_{1-4}$ alkoxycarbonyl groups, hydroxyl group, mercapto group, carboxyl group, amino group, N—C$_{1-4}$ alkylamino groups, N,N-di-C$_{1-4}$ alkylamino groups, cyano group, halo-C$_{1-4}$ alkyl groups, unsubstituted or halogen-substituted phenyl groups, unsubstituted or halogen-substituted naphthyl groups, unsubstituted or halogen-substituted formyl groups, unsubstituted or halogen-substituted C$_{2-10}$ alkanoyl groups unsubstituted or halogen-substituted benzoyl groups and unsubstituted or C$_{1-10}$ alkyl-, C$_{3-8}$ cycloalkyl-, phenyl- or naphthyl-substituted carbamoyl groups.

4. The triazole derivative or its salt according to claim 1, wherein R$^1$ represents a phenyl or naphthyl group which may be optionally substituted by a halogen atom, a C$_{1-4}$ alkyl group, a C$_{1-4}$ alkoxy group, a halo-C$_{1-4}$ alkoxy group; R$^2$ represents a fluorine atom; R$^3$ represents a group of the formula

in which R$^4$ is a group of the formula

($R^7$ and $R^8$, which may be the same or different, are hydrogen atoms; $C_{1-10}$ alkyl groups which may be optionally substituted by a halogen atom, a $C_{1-4}$ alkoxy group, a $C_{1-4}$ alkylthio group, a $C_{1-4}$ alkoxycarbonyl group, a hydroxyl group, a mercapto group, a carboxyl group, an N,N-di-$C_{1-4}$ alkylamino group, a cyano group, a halogen-substituted phenyl group or a $C_{3-8}$ cycloalkyl-substituted carbamoyl group; $C_{2-10}$ alkenyl groups; $C_{2-10}$ alkynyl groups; $C_{3-8}$ cycloalkyl groups which may be optionally substituted by a $C_{1-4}$ alkyl group or a halogen-substituted phenyl group; phenyl groups which may be optionally substituted by a halogen atom, an unsubstituted or cyano-substituted $C_{1-4}$ alkyl group, a halo- $C_{1-4}$ alkyl group, a $C_{1-4}$ alkoxy group, a hydroxyl group or a cyano group; amino groups which may be optionally substituted by a halogen-substituted benzoyl group; hydroxyl group; $C_{1-4}$ alkoxy groups or a phenyl-substituted carbamoyl group.

5. The triazole derivative or its salt according to claim 1, wherein $R^1$ represents a phenyl group which may be optionally substituted by a halogen atom; $R^2$ represents a fluorine atom; and $R^3$ represents a group of the formula

in which $R^4$ is a group of the formula

($R^7$ and $R^8$, which may be the same or different, are hydrogen atoms; $C_{1-10}$ alkyl groups which may be optionally substituted by a halogen atom, a $C_{1-4}$ alkoxy group, a $C_{1-4}$ alkylthio group, a $C_{1-4}$ alkoxycarbonyl group, a hydroxyl group, a mercapto group, a carboxyl group, an N,N-di-$C_{1-4}$ alkylamino group, a cyano group, a halogen-substituted phenyl group or a $C_{3-8}$ cycloalkyl-substituted carbamoyl group; $C_{2-10}$ alkenyl groups; $C_{2-10}$ alkynyl groups; $C_{3-8}$ cycloalkyl groups which may be optionally substituted by a $C_{1-4}$ alkyl group or a halogen-substituted phenyl group; phenyl groups which may be optionally substituted by a halogen atom, a $C_{1-4}$ alkyl group, a $C_{1-4}$ alkoxy group, a hydroxyl group or a cyano group; amino groups which may be optionally substituted by a halogen-substituted benzoyl group; hydroxyl group; $C_{1-4}$ alkoxy groups).

6. The triazole derivative or its salt according to claim 5, wherein $R^3$ represents a group of the formula:

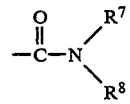

in which one of $R^7$ and $R^8$ is a hydrogen atom and the other is a hydrogen atom; an $C_{1-10}$ alkyl group which may be optionally substituted by a halogen atom, a $C_{1-4}$ alkoxy group, a $C_{1-4}$ alkylthio group, a $C_{1-4}$ alkoxycarbonyl group, a hydroxyl group, a mercapto group, a carboxyl group, an N,N-di-$C_{1-4}$ alkylamino group, a cyano group, a halogen-substituted phenyl group or a $C_{3-8}$ cycloalkyl-substituted carbamoyl group; an $C_{2-10}$ alkenyl group; an $C_{2-10}$ alkynyl group; a $C_{3-8}$ cycloalkyl group which may be optionally substituted by a $C_{1-4}$ alkyl group or a halogen-substituted phenyl group; a phenyl group which may be optionally substituted by a halogen atom, a $C_{1-4}$ alkyl group, a $C_{1-4}$ alkoxy group, a hydroxyl group or a cyano group; an amino group which may be optionally substituted by a halogen-substituted benzoyl group; a hydroxyl group or a $C_{1-4}$ alkoxy group.

7. The triazole derivative or its salt according to claim 6, wherein $R^1$ represents a halogen-substituted phenyl group and $R^2$ represents a fluorine atom.

8. The triazole derivative or its salt according to claim 7, wherein one of $R^7$ and $R^8$ is a hydrogen atom and the other is a hydrogen atom, a $C_{1-4}$ alkyl group or a cyclopropyl group.

9. The triazole derivative or its salt according to claim 7, wherein the halogen-substituted phenyl group is a 2,4-difluorophenyl group or a 2-chloro-4-fluorophenyl group.

10. The triazole derivative or its salt according to claim 9, wherein one of $R^7$ and $R^8$ is a hydrogen atom and the other is a hydrogen atom, a methyl group or a cyclopropyl group.

11. N-methyl-3-(2,4-difluorophenyl)-2,2-difluoro-3-hydroxy-4-(1H-1,2,4-triazol-1-yl)butanamide or its salt.

12. (—)-N-methyl-3-(2,4-difluorophenyl)-2,2-difluoro-3-hydroxy-4-(1H-1,2,4-triazol-1-yl)butanamide or its salt.

13. 3-(2,4-Difluorophenyl)-2,2-difluoro-3-hydroxy-4-(1H-1,2,4-triazol-1-yl)butanamide or its salt.

14. (—)-3-(2,4-Difluorophenyl)-2,2-difluoro-3-hydroxy-4-(1H-1,2,4-triazol-1-yl)butanamide or its salt.

15. 3-(2-Chloro-4-fluorophenyl)-2,2-difluoro-3-hydroxy-4-(1H-1,2,4-triazol-1-yl)butanamide or its salt.

16. (—)-3-(2-Chloro-4-fluorophenyl)-2,2-difluoro-3-hydroxy-4-(1H-1,2,4-triazol-1-yl)butanamide or its salt.

17. N-methyl-3-(2-chloro-4-fluorophenyl)-2,2-difluoro-3-hydroxy-4-(1H-1,2,4-triazol-1-yl)butanamide or its salt.

18. (—)-N-methyl-3-(2-chloro-4-fluorophenyl)-2,2-difluoro-3-hydroxy-4-(1H-1,2,4-triazol-1-yl)butanamide or its salt.

19. N-cyclopropyl-3-(2,4-difluorophenyl)-2,2-difluoro-3-hydroxy-4-(1H-1,2,4-triazol-1-yl)butanamide or its salt.

20. (—)-N-cyclopropyl-3-(2,4-difluorophenyl)-2,2-difluoro-3-hydroxy-4-(1H-1,2,4-triazol-1-yl)butanamide or its salt.

21. An antifungal composition comprising an effective amount of a triazole derivative as in any of claims 1-19 or 20 and a pharmaceutically acceptable carrier, excipient or diluent.

* * * * *